(12) United States Patent
Hanzawa et al.

(10) Patent No.: US 9,175,346 B2
(45) Date of Patent: Nov. 3, 2015

(54) EVALUATION METHOD FOR ARTERIOSCLEROSIS

(75) Inventors: Hiroko Hanzawa, Tokorozawa (JP); Takeshi Sakamoto, Asaka (JP); Naomi Manri, Kawagoe (JP); Yuji Kuge, Sapporo (JP)

(73) Assignee: Hitachi, Ltd., Tokyo (JP)

( * ) Notice: Subject to any disclaimer, the term of this patent is extended or adjusted under 35 U.S.C. 154(b) by 288 days.

(21) Appl. No.: 13/643,590

(22) PCT Filed: Apr. 19, 2011

(86) PCT No.: PCT/JP2011/059591
§ 371 (c)(1),
(2), (4) Date: Oct. 26, 2012

(87) PCT Pub. No.: WO2011/136080
PCT Pub. Date: Nov. 3, 2011

(65) Prior Publication Data
US 2013/0040851 A1    Feb. 14, 2013

(30) Foreign Application Priority Data
Apr. 28, 2010   (JP) ................................ 2010-103672

(51) Int. Cl.
| G01N 31/00 | (2006.01) |
| G01N 33/53 | (2006.01) |
| C12Q 1/68 | (2006.01) |
| G01N 33/564 | (2006.01) |
| G01N 33/86 | (2006.01) |
| G01N 33/18 | (2006.01) |

(52) U.S. Cl.
CPC .......... *C12Q 1/6883* (2013.01); *G01N 33/1826* (2013.01); *G01N 33/564* (2013.01); *G01N 33/86* (2013.01); *C12Q 2600/112* (2013.01); *C12Q 2600/158* (2013.01); *G01N 33/18* (2013.01); *G01N 2333/4716* (2013.01); *G01N 2800/323* (2013.01); *G01N 2800/50* (2013.01); *G01N 2800/52* (2013.01)

(58) Field of Classification Search
CPC ...... G01B 5/012; G01B 7/002; B23Q 3/1554; B23Q 3/15526; G01N 33/6893; G01N 2800/52; G01N 2800/323
See application file for complete search history.

(56) References Cited

U.S. PATENT DOCUMENTS

| 7,998,682 B2 | 8/2011 | Hwang et al. |
| 2002/0164662 A1 | 11/2002 | Hazen et al. |
| 2009/0149643 A1 | 6/2009 | Diener et al. |

FOREIGN PATENT DOCUMENTS

| JP | 2007-278907 A | 10/2007 |
| JP | 2008-67715 A | 3/2008 |
| JP | 2008-512094 A | 4/2008 |
| JP | 2008-512098 A | 4/2008 |
| WO | WO 02/062207 A2 | 8/2002 |
| WO | WO 2006/029052 A2 | 3/2006 |
| WO | WO 2006/033854 A2 | 3/2006 |
| WO | WO 2008/106644 A2 | 9/2008 |

OTHER PUBLICATIONS

Platform GPL1261 , printed from http://www.ncbi.nlm.nih.gov/geo/query/acc.cgi?acc=GPL1261 as pp. 1/3-3/3 on Oct. 1, 2014, publicly available May 25, 2004, and including a partial gene list showing probes for VWF, CFD, C8B, and PROZ.*
Grabner et al. Lymphotoxin beta receptor signaling promoters tertiary lymphoid oranogenesis in the aora adventitia of aged ApoE^ -/- mice. The Journal of Experimental Medicine, vol. 206, No. 1, pp. 233-248, Jan. 12, 2009.*
GEO accession No. GSE10000, printed from http://www.ncbi.nlm.nih.gov/geo/query/acc.cgi?acc=GSE10000 on Oct. 1, 2014 as pp. 1/3-3/3, publicly available on Dec. 16, 2008.*
Speidl et al. Journal of Thrombosis and Haemostasis, vol. 9, pp. 428-440, 2011.*
English Translation of Written Opinion dated May 31, 2011 (PCT/ISA/237) (four (4) pages).
Japanese Office Action with English Translation dated Jan. 22, 2013 (six (6) pages).
International Search Report with English translation dated May 31, 2011 (five (5) sheets).
Form PCT/ISA/237 (three (3) sheets).

(Continued)

*Primary Examiner* — Lisa Cook
(74) *Attorney, Agent, or Firm* — Crowell & Moring LLP

(57) ABSTRACT

Arteriosclerosis induces cerebral infarction and myocardial infarction. A multi-marker (a group of protein markers) that assesses the accurate pathogenesis of arteriosclerosis and enables the selection of an adequate treatment method for arteriosclerosis and prediction of the progression of arteriosclerosis, and an evaluation method for the diagnosis, prevention, and treatment of arteriosclerosis that uses said marker group as an indicator have been sought. The present invention relates to A method for evaluation of arteriosclerosis comprising the steps of (a) measuring the expression of von Willebrand factor and/or complement factor D in a sample derived from a subject, (b) measuring the expression of complement component C8 and/or vitamin K-dependent protein Z in the sample derived from the subject, and (c) evaluating arteriosclerosis in the subject on the basis of the results from (a) and (b).

13 Claims, 14 Drawing Sheets

(56) References Cited

OTHER PUBLICATIONS

Naito et al., "Significance of von Willebrand Factor as a Marker for Asymptomatic Atherosclerosis in a Carotid Artery", Japanese Journal of Applied Physiology, 1999, vol. 29, No. 3, pp. 181-186 (six (6) sheets).

Fujii et al., "Atarashii Domyaku Koka Kiken Marker to Sono Igi Fibrinogen", vWF, PAI-I, Prog. Med. 1999, vol. 19, No. 8, pp. 1864-1868 (five (5) sheets).

Murata, "Ketsueki Gyoko Ijosho ni Kansuru Chosa Kenkyu ADAMTSI3 to Kessensho", Ketsueki Gyoko Ijosho ni Kansuru Chosa Kenkyu Heisel 16 Nendo Sokatsu-Buntan Kenkyu Hokokusho, 2005, pp. 115-120 (six(6) sheets).

Ihara et al., "Kyoketsusei Shinsikkan ni Okeru Kessenshiketsu Inshi to Kesshoban Shisu no Kanren", Journal of the Hiroshima Medical Association, 2006, vol. 59, No. 9, pp. 713-718 (seven (7) sheets).

Yasojima et al., Complement Components, but Not Complement Inhibitors, Are Upregulated in Atherosclerotic Plaques, Arterioscler Thromb Vasc Biol, 2001, vol. 21, No. 7, pp. 1214-1219 (six (6) sheets).

Oda et al., "Analysis of Protein Absorbed by LDL col. (Liposorber) with Special Reference to Complement Component Factor D", Clinic. Chimica Acta, 2004, vol. 342, Nos. 1-2, pp. 155-160 (six (6) sheets).

Packard et al., "Inflammation in Atherosclerosis: From Vascular Biology to Biomarker Discovery and Risk Prediction", Clinical Chemistry, 2008, vol. 54, No. 1, pp. 24-38 (fifteen (15) sheets).

Hanash, "Disease Proteomics", Insight Review Articles, Nature, Mar. 13, 2003, vol. 422, pp. 226-232 (seven (7) sheets).

* cited by examiner

Category 1

A

| Origin of tissue | Entry name (sex) | Expression ratio (ApoE-deficient/wild-type) | | | |
|---|---|---|---|---|---|
| | | stage 1 (12-week-old) | stage 2 (18-week-old) | stage 3 (25-week-old) | stage 4 (35-week-old) |
| Plasma | CO8A_MOUSE (M) | 1.281 | 1.250 | 1.377 | 1.855 |
| | CO8B_MOUSE (M) | 1.284 | 1.263 | 1.370 | 1.931 |
| | CO8G_MOUSE (M) | 1.293 | 1.211 | 1.356 | 1.870 |
| | IGHM_MOUSE (F) | | 3.244 | 4.815 | 5.002 |
| | C1QB_MOUSE (M) | 0.978 | 1.127 | 1.243 | 1.239 |
| | FETUB_MOUSE (F) | 0.922 | 0.897 | 1.035 | 1.197 |
| | CFAH_MOUSE (F) | 0.997 | 1.116 | 1.265 | 1.174 |

B

Category 2

A

| Origin of tissue | Entry name (sex) | Expression ratio (ApoE-deficient/wild-type) | | | |
|---|---|---|---|---|---|
| | | stage 1 (12-week-old) | stage 2 (18-week-old) | stage 3 (25-week-old) | stage 4 (35-week-old) |
| Plasma | ITIH1_MOUSE (M) | 1.339 | 1.159 | 0.924 | 0.951 |
| | ITIH2_MOUSE (M) | 1.331 | 1.165 | 0.994 | 1.039 |
| | PROP_MOUSE (M) | 2.445 | 1.796 | 1.433 | 1.485 |
| | PROP_MOUSE (F) | 2.095 | 2.174 | 1.562 | 1.433 |
| | PROZ_MOUSE (F) | 1.079 | 1.048 | 0.885 | 0.886 |
| | A2M_MOUSE (M) | 1.443 | 1.278 | 1.163 | 1.059 |
| | PROC_MOUSE (M) | 1.261 | 1.067 | 0.955 | 0.558 |
| | CO9_MOUSE (M) | 1.203 | 1.105 | 1.001 | 1.000 |
| | ANT3_MOUSE (M) | 0.997 | 0.844 | 0.791 | |
| | FBLN3_MOUSE (M) | 1.313 | 1.196 | 1.089 | 1.013 |
| | HEP2_MOUSE (M) | 1.050 | 1.016 | 0.882 | 0.790 |

B

Category 3

A

| Origin of tissue | Entry name (sex) | Expression ratio (ApoE-deficient/wild-type) | | | |
|---|---|---|---|---|---|
| | | stage 1 (12-week-old) | stage 2 (18-week-old) | stage 3 (25-week-old) | stage 4 (35-week-old) |
| Plasma | CD5L_MOUSE (M) | 5.441 | 6.885 | 4.618 | 3.306 |
| | IGHM_MOUSE (M) | 6.114 | 6.717 | 4.114 | 3.758 |
| | VWF_MOUSE (M) | 1.075 | 1.299 | 0.899 | 1.000 |
| | HEP2_MOUSE (F) | 1.146 | 1.303 | 0.848 | 0.791 |
| | ANT3_MOUSE (F) | 0.853 | 1.063 | 0.778 | 0.757 |
| | CO9_MOUSE (F) | 1.116 | 1.760 | 1.190 | 1.204 |
| | PROC_MOUSE (F) | 1.131 | 1.499 | 0.971 | 0.832 |
| | A2M_MOUSE (F) | 1.202 | 1.321 | 1.132 | 0.983 |
| | FBLN3_MOUSE (F) | 1.072 | 1.263 | 1.044 | 1.010 |
| | C1QB_MOUSE (F) | 1.258 | 1.977 | 1.538 | 1.683 |
| | ITIH1_MOUSE (F) | 1.026 | 1.094 | 1.000 | 0.900 |
| | ITIH2_MOUSE (F) | 0.998 | 1.077 | 0.969 | 0.896 |

B

Category 4

A

| Origin of tissue | Entry name (sex) | Expression ratio (ApoE-deficient/wild-type) | | | |
| --- | --- | --- | --- | --- | --- |
| | | stage 1 (12-week-old) | stage 2 (18-week-old) | stage 3 (25-week-old) | stage 4 (35-week-old) |
| Plasma | CFAD_MOUSE (M) | 1.079 | 0.968 | 1.039 | |
| | CFAD_MOUSE (F) | 1.010 | 0.845 | 1.225 | 1.250 |
| | FETUB_MOUSE (M) | 1.111 | 0.977 | 0.982 | 1.305 |

B

Category 5

A

| Origin of tissue | Entry name (sex) | Expression ratio (ApoE-deficient/wild-type) | | | |
|---|---|---|---|---|---|
| | | stage 1 (12-week-old) | stage 2 (18-week-old) | stage 3 (25-week-old) | stage 4 (35-week-old) |
| Plasma | PROZ_MOUSE (M) | 1.038 | 0.943 | 1.521 | 0.569 |
| | CO8A_MOUSE (F) | 1.241 | 1.851 | 2.584 | 2.124 |
| | CO8B_MOUSE (F) | 1.245 | 1.824 | 2.404 | 2.098 |
| | CO8G_MOUSE (F) | 1.319 | 2.132 | 2.206 | 1.903 |
| | CD5L_MOUSE (F) | 3.634 | 4.341 | 4.782 | 4.613 |

B

Category 6

A

| Origin of tissue | Entry name (sex) | Expression ratio (ApoE-deficient/wild-type) | | | |
|---|---|---|---|---|---|
| | | stage 1 (12-week-old) | stage 2 (18-week-old) | stage 3 (25-week-old) | stage 4 (35-week-old) |
| Plasma | TSP4_MOUSE (M) | 1.112 | 0.951 | 0.935 | 1.118 |
| | TSP4_MOUSE (F) | 1.235 | 1.330 | 0.912 | 1.367 |
| | IC1_MOUSE (M) | 0.838 | 0.792 | 0.664 | 0.856 |
| | CFAH_MOUSE (M) | 1.052 | 1.125 | 0.818 | 1.190 |

B

A

| Entry name (sex) | 12wk | 18wk | 25wk | 35wk | Features |
|---|---|---|---|---|---|
| VWF_MOUSE (M) | 1.075 | 1.299 | 0.899 | 1.000 | Maximum at 18-week-old |
| CFAD_MOUSE (F) | 1.010 | 0.845 | 1.225 | 1.250 | Minimum at 18-week-old |
| CO8A_MOUSE (F) | 1.241 | 1.851 | 2.584 | 2.124 | Maximum at 25-week-old |
| PROZ_MOUSE (M) | 1.038 | 0.943 | 1.521 | 0.569 | Maximum at 25-week-old |

B

A

| Entry name (sex) | 12wk | 18wk | 25wk | 35wk |
|---|---|---|---|---|
| TSP4_MOUSE (F) | 1.235 | 1.330 | 0.912 | 1.367 |
| CFAH_MOUSE (M) | 1.052 | 1.125 | 0.818 | 1.190 |
| IC1_MOUSE (M) | 0.838 | 0.792 | 0.664 | 0.856 |

B

A

| Entry name (sex) | 12wk | 18wk | 25wk | 35wk |
|---|---|---|---|---|
| PROP_MOUSE (F) | 2.095 | 2.174 | 1.562 | 1.433 |
| A2M_MOUSE (M) | 1.443 | 1.278 | 1.163 | 1.059 |
| HEP2_MOUSE (M) | 1.050 | 1.016 | 0.882 | 0.790 |
| PROC_MOUSE (M) | 1.261 | 1.067 | 0.955 | 0.558 |
| PROP_MOUSE (M) | 2.445 | 1.796 | 1.433 | 1.485 |

| Priority | Protein description | Entry name | Mouse/female | | | | Mouse of another line/female | (Mouse at each age in weeks – mouse of another line)^2 | | | |
|---|---|---|---|---|---|---|---|---|---|---|---|
| | | | 12wk | 18wk | 25wk | 35wk | | 12wk | 18wk | 25wk | 35wk |
| 1 | von Willebrand factor | VWF_MOUSE | 0.948 | 1.612 | 0.799 | 1.287 | 1.507 | 0.215 | 0.005 | 0.403 | 0.025 |
| 1 | Complement factor D | CFAD_MOUSE | 1.010 | 0.845 | 1.225 | 1.250 | 0.930 | 0.007 | 0.009 | 0.076 | 0.088 |
| 1 | Complement component C8 alpha chain | CO8A_MOUSE | 1.241 | 1.851 | 2.584 | 2.124 | 0.944 | 0.075 | 0.453 | 1.013 | 0.657 |
| 1 | Complement component C8 beta chain | CO8B_MOUSE | 1.245 | 1.824 | 2.404 | 2.098 | 0.978 | 0.058 | 0.389 | 0.809 | 0.583 |
| 1 | Complement component C8 gamma chain | CO8G_MOUSE | 1.319 | 2.132 | 2.206 | 1.903 | 0.946 | 0.110 | 0.660 | 0.717 | 0.488 |
| 1 | Vitamin K-dependent protein Z | PROZ_MOUSE | 1.079 | 1.048 | 0.885 | 0.886 | 1.273 | 0.027 | 0.038 | 0.132 | 0.132 |
| 2 | CD5 antigen-like | CD5L_MOUSE | 3.634 | 4.341 | 4.782 | 4.613 | 2.308 | 0.206 | 0.399 | 0.531 | 0.480 |
| 2 | Ig mu chain C region membrane-bound form | MUCM_MOUSE | 1.844 | 3.359 | 4.791 | 5.018 | 2.815 | 0.179 | 0.031 | 0.283 | 0.334 |
| 2 | Heparin cofactor 2 | HEP2_MOUSE | 1.146 | 1.303 | 0.848 | 0.791 | 1.017 | 0.014 | 0.061 | 0.033 | 0.063 |
| 2 | Plasma protease C1 inhibitor | IC1_MOUSE | 0.835 | 0.978 | 1.026 | 0.925 | | | | | |
| 2 | Thrombospondin-4 | TSP4_MOUSE | 1.235 | 1.330 | 0.912 | 1.367 | 1.882 | 0.177 | 0.120 | 0.525 | 0.102 |
| 3 | Alpha-2-macroglobulin | A2M_MOUSE | 1.202 | 1.321 | 1.132 | 0.983 | 1.289 | 0.005 | 0.001 | 0.017 | 0.074 |
| 3 | Complement component C9 | CO9_MOUSE | 1.116 | 1.760 | 1.190 | 1.204 | 0.998 | 0.013 | 0.322 | 0.031 | 0.035 |
| 3 | Fetuin-B | FETUB_MOUSE | 0.922 | 0.897 | 1.035 | 1.197 | 1.062 | 0.020 | 0.028 | 0.001 | 0.014 |
| 3 | Vitamin K-dependent protein C | PROC_MOUSE | 1.131 | 1.499 | 0.971 | 0.832 | 1.202 | 0.004 | 0.049 | 0.046 | 0.135 |
| 4 | Antithrombin-III | ANT3_MOUSE | 0.853 | 1.063 | 0.778 | 0.757 | 0.902 | 0.003 | 0.027 | 0.022 | 0.030 |
| 4 | Complement C1q subcomponent subunit B | C1QB_MOUSE | 1.258 | 1.977 | 1.538 | 1.683 | 0.897 | 0.114 | 0.625 | 0.290 | 0.396 |
| 4 | Complement factor H | CFAH_MOUSE | 0.997 | 1.116 | 1.265 | 1.174 | 0.999 | 0.000 | 0.012 | 0.056 | 0.026 |
| 4 | EGF-containing fibulin-like extracellular matrix protein 1 | FBLN3_MOUSE | 1.072 | 1.263 | 1.044 | 1.010 | 1.002 | 0.005 | 0.054 | 0.002 | 0.000 |
| 4 | Inter-alpha-trypsin inhibitor heavy chain H1 | ITIH1_MOUSE | 1.026 | 1.094 | 1.000 | 0.900 | 0.973 | 0.003 | 0.014 | 0.001 | 0.006 |
| 4 | Inter-alpha-trypsin inhibitor heavy chain H2 | ITIH2_MOUSE | 0.998 | 1.077 | 0.969 | 0.896 | 1.070 | 0.005 | 0.000 | 0.010 | 0.032 |
| 4 | Properdin | PROP_MOUSE | 2.095 | 2.174 | 1.562 | 1.433 | 1.829 | 0.019 | 0.030 | 0.025 | 0.059 |

Ratios of protein expression levels in disease mice to the same in healthy mice

Ratios of protein expression levels in disease mice of another line to the same in healthy mice

| | 12wk | 18wk | 25wk | 35wk | |
|---|---|---|---|---|---|
| | 0.082 | 0.259 | 0.525 | 0.329 | Priority No. 1 alone |
| | 0.107 | 0.217 | 0.452 | 0.295 | Priority No. 1 and 2 |
| | 0.079 | 0.183 | 0.330 | 0.229 | Priority No. 1, 2, and 3 |
| | 0.060 | 0.158 | 0.239 | 0.179 | All proteins |

Mean square sum of differences between logarithms of ratios in protein expression levels in mice at each age in weeks and the same in mice of another line

Fig. 12

| Priority | Protein description | Entry name | 12F | 18F | 25F | 35F | 12M | 18M | 25M | 35M |
|---|---|---|---|---|---|---|---|---|---|---|
| 1 | von Willebrand factor | VWF_MOUSE | 0.171 | 0.014 | 0.341 | 0.012 | 0.127 | 0.028 | 0.287 | 0.184 |
| 1 | Complement factor D | CFAD_MOUSE | 0.315 | 0.147 | 0.570 | 0.600 | | | | |
| 1 | Complement component C8 alpha chain | CO8A_MOUSE | 0.401 | 1.067 | 1.867 | 1.370 | 0.242 | 0.219 | 0.318 | 0.744 |
| 1 | Complement component C8 beta chain | CO8B_MOUSE | 0.309 | 0.880 | 1.474 | 1.161 | 0.096 | 0.086 | 0.141 | 0.515 |
| 1 | Complement component C8 gamma chain | CO8G_MOUSE | 0.320 | 1.094 | 1.167 | 0.869 | 0.146 | 0.101 | 0.185 | 0.565 |
| 1 | Vitamin K-dependent protein Z | PROZ_MOUSE | 0.003 | 0.000 | 0.022 | 0.022 | 0.767 | 0.944 | 0.244 | 2.180 |
| 1 | CD5 antigen-like | CD5L_MOUSE | 1.360 | 1.806 | 2.076 | 1.974 | 1.440 | 2.060 | 1.073 | 0.492 |
| 1 | Ig mu chain C region | IGHM_MOUSE | | | | | 1.114 | 1.321 | 0.435 | 0.323 |
| 2 | Heparin cofactor 2 | HEP2_MOUSE | 0.304 | 0.462 | 0.063 | 0.033 | 0.035 | 0.024 | 0.000 | 0.009 |
| 2 | Plasma protease C1 inhibitor | IC1_MOUSE | 0.003 | 0.046 | 0.069 | 0.025 | 0.056 | 0.032 | 0.000 | 0.066 |
| 2 | Thrombospondin-4 | TSP4_MOUSE | 0.471 | 0.578 | 0.146 | 0.620 | 0.005 | 0.050 | 0.058 | 0.004 |
| 2 | Alpha-2-macroglobulin | A2M_MOUSE | 0.147 | 0.229 | 0.105 | 0.033 | 0.857 | 0.646 | 0.504 | 0.379 |
| 3 | Complement component C9 | CO9_MOUSE | 0.103 | 0.602 | 0.148 | 0.157 | 0.366 | 0.270 | 0.177 | 0.176 |
| 3 | Fetuin-B | FETUB_MOUSE | 0.144 | 0.124 | 0.245 | 0.410 | 0.024 | 0.001 | 0.001 | 0.099 |
| 3 | Vitamin K-dependent protein C | PROC_MOUSE | 0.004 | 0.049 | 0.045 | 0.134 | 0.003 | 0.012 | 0.048 | 0.574 |
| 4 | Antithrombin-III | ANT3_MOUSE | 0.006 | 0.020 | 0.029 | 0.039 | | | | |
| 4 | Complement C1q subcomponent subunit B | C1QB_MOUSE | 0.307 | 1.012 | 0.569 | 0.714 | 1.228 | 1.561 | 1.816 | 1.808 |
| 4 | Complement factor H | CFAH_MOUSE | 0.022 | 0.068 | 0.150 | 0.098 | 0.026 | 0.052 | 0.008 | 0.081 |
| 4 | EGF-containing fibulin-like extracellular matrix protein | FBLN3_MOUSE | 0.066 | 0.177 | 0.052 | 0.039 | 0.351 | 0.249 | 0.164 | 0.111 |
| 4 | Inter-alpha-trypsin inhibitor heavy chain H1 | ITIH1_MOUSE | 0.038 | 0.067 | 0.029 | 0.004 | 0.074 | 0.016 | 0.010 | 0.005 |
| 4 | Inter-alpha-trypsin inhibitor heavy chain H2 | ITIH2_MOUSE | | 0.860 | 0.356 | 0.261 | 0.002 | 0.008 | 0.061 | 0.041 |
| 4 | Properdin | PROP_MOUSE | 0.793 | | | | 0.864 | 0.386 | 0.156 | 0.186 |
| | | | 5.286 | 9.304 | 9.523 | 8.574 | 7.822 | 8.067 | 5.687 | 8.543 |
| | | | 0.264 | 0.465 | 0.476 | 0.429 | 0.391 | 0.403 | 0.284 | 0.427 |

Mean square sum of differences between logarithms of ratios of protein expression levels in mice at each age in weeks and the same in humans (Mouse at each age in weeks − human)^2

EVALUATION METHOD FOR ARTERIOSCLEROSIS

TECHNICAL FIELD

The present invention relates to a method, a kit, and an apparatus for evaluating arteriosclerosis. More specifically, the present invention relates to a method for evaluation of arteriosclerosis based on the expression of marker protein(s). Furthermore, the present invention relates to an evaluation method for evaluating the effectiveness of therapeutic agents or treatment methods for arteriosclerosis.

BACKGROUND ART

The term "arteriosclerosis" is a general term for diseases characterized by arterial wall thickening caused by a variety of factors such as aging and lifestyle habits, decreased artery elasticity, and inner-cavity stenosis. Arteriosclerosis proceeds over a long period of time without subjective symptoms, inducing cardiac diseases such as myocardial infarction or cerebrovascular diseases such as cerebral infarction or cerebral-hemorrhage. Therefore, it is important to develop a method for conveniently and accurately assaying with certainty the severity and the extent of arteriosclerosis and therapeutic effects against arteriosclerosis. Conventionally, assays using as indicators, in addition to blood pressure levels or lipid marker levels (total serum cholesterol level, high LDL cholesterol level, and low HDL cholesterol level), blood concentrations of inflammatory markers including a high sensitive C-reactive protein (hs-CRP), serum amyloid A (SAA), an oxidant stress-related factor homocystine, and the like have been examined in many epidemiological studies. However, since the levels of these factors vary in other diseases, a search for a more selective marker with high disease specificity has been an issue. Arteriosclerosis follows the multifaceted processes of lipid deposition in vascular intima, inflammatory cell infiltration, smooth muscle cell proliferation, foam cell formation of macrophage and/or smooth muscle cells, interstitial matrix formation, and the like. It has been demonstrated that in each process, various factors are synergistically involved in progression of lesions (Non-patent document 1). An assay with a combination of a plurality of markers is thought to be effective for accurately assessing pathogenesis.

Disease proteomics is a technique for exhaustively searching for an increase or a decrease in protein level, which varies depending on the specific disease, compared with a healthy state, using a body fluid such as blood, saliva, or urine, or a tissue sample, as a material. Disease proteomics is characterized by being capable of simultaneously extracting and/or detecting a plurality of factors with unknown relationships to the disease. Application of multiple specimens to and increased sensitivity of a 2D electrophoresis method and measuring apparatuses such as a protein microarray and mass spectrometry have been realized, and data analysis technology has been in place, which have been applied for searching markers for various diseases including cancer, immunity disorders, infections, and the like (Non-patent document 2).

PRIOR ART DOCUMENTS

Non-Patent Documents

Non-patent document 1 Packard R. R. and Libby P., Clinical Chemistry, Vol. 54, pp. 24-38, 2008

Non-patent document 2 Hanash S., Nature, Vol. 422, pp. 226-232, 2003

SUMMARY OF THE INVENTION

Problem to be Solved by the Invention

Arteriosclerosis is developed not only in middle-aged and older people, but also in young people, along with current lifestyle or social structural changes, for example. Thus, diagnosis and prevention of the onset of arteriosclerosis are important issues. Precise evaluation of arteriosclerosis would enable prevention of the disease through improvement of lifestyle or the like, early diagnosis, prevention of progression and/or worsening of the disease, and treatment of the disease. This will help the realization of healthy life while giving us clues to resolving the social problems of a super-aging society, such as expected reduction of financial burden due to increasing medical costs. Therefore, development of a technology capable of specifically predicting and/or determining precisely the presence or the absence of arteriosclerosis, or the progression of arteriosclerosis is required.

Therefore, an object of the present invention is to provide an evaluation method for diagnosis, prevention, or treatment of arteriosclerosis by identifying the expression patterns of maker proteins with a proteomic technique which varies with the progression of arteriosclerosis, recording the variation into an expression profile database, comparing the data with the variation in the expression of the protein group in samples obtained from subjects, and thereby identifying the stage of progression of arteriosclerosis.

Means for Solving the Problem

The present inventors have obtained plasma from ApoE-deficient mice, in which arteriosclerosis commonly occurs and the progression thereof is accelerated by administration of high-fat diet and aging (age in weeks), and wild-type mice, and then exhaustively compared and analyzed the expression levels of proteins contained in plasma with mass spectrometry. An expression profile database was constructed by using the measured values of the ratios of the expression levels of proteins contained in plasma obtained at each age in weeks (12-week-old, 18-week-old, 25-week-old, and 35-week-old) differing in the extent of arteriosclerosis. It was discovered that the onset or the progression (worsening) of arteriosclerosis correlates with a variation tendency in each protein expression ratio, and the tendencies can be classified into a plurality of groups. Furthermore, the present inventors have succeeded in identifying proteins that exhibit expression tendencies characteristic of specific arteriosclerosis stages, and have found that the proteins can be used as markers for evaluation of the likelihood of the onset of arteriosclerosis, high or low risk of the disease, and possibility of progression, thereby having completed the present invention.

The present invention provides the following [1] to [23].

[1] A method for evaluation of arteriosclerosis, comprising the steps of:
 (a) measuring the expression of von Willebrand factor and/or complement factor D in a subject-derived sample;
 (b) measuring the expression of complement component C8 and/or vitamin K-dependent protein Z in the subject-derived sample; and
 (c) evaluating arteriosclerosis of the subject based on the results of (a) and (b).

[2] The method according to [1], comprising further measuring the expression of at least one selected from the group consisting of a CD5 antigen-like protein, Ig μ chain C region, heparin cofactor 2, a plasma protease C1 inhibitor, and thrombospondin-4 in the subject-derived sample.

[3] The method according to [1] or [2], comprising further measuring the expression of at least one selected from the group consisting of α-2-macroglobulin, complement component C9, fetuin-B, and vitamin K-dependent protein C in the subject-derived sample.

[4] The method according to any one of [1] to [3], comprising further measuring the expression of at least one selected from the group consisting of antithrombin-III, complement C1 q subcomponent subunit B, complement factor H, EGF-containing fibrin-like extracellular matrix protein 1, inter alpha trypsin inhibitor heavy chain H1, inter alpha trypsin inhibitor heavy chain H2, and properdin in the subject-derived sample.

[5] The method according to any one of [1] to [4], wherein the evaluation of arteriosclerosis is determination of the presence of arteriosclerosis in the subject, determination of the stage of arteriosclerosis existing in the subject, evaluation of a therapeutic effect against arteriosclerosis existing in the subject, or prediction of prognosis of arteriosclerosis existing in the subject.

[6] A method for evaluation of arteriosclerosis, comprising the steps of:
(a) measuring the expression of von Willebrand factor and/or complement factor D in a subject-derived sample; and
(b) evaluating whether or not the subject has arteriosclerosis at the early intermediate stage based on the result of (a).

[7] A method for evaluation of arteriosclerosis, comprising the steps of:
(a) measuring the expression of complement component C8 and/or vitamin K-dependent protein Z in a subject-derived sample; and
(b) evaluating whether or not the subject has arteriosclerosis at the intermediate stage based on the result of (a).

[8] The method according to any one of [1] to [7], wherein the evaluation step comprises comparing with a standard level selected from the measured expression level in a sample of a healthy subject, and the measured expression level in a sample of a subject with arteriosclerosis at a known stage.

[9] The method according to any one of [1] to [6] and [8], wherein an expression level of the von Willebrand factor that is higher than the standard level indicates the presence of arteriosclerosis at the early intermediate stage in the subject.

[10] The method according to any one of [1] to [6], [8] and [9], wherein an expression level of complement factor D that is lower than the standard level indicates the presence of arteriosclerosis at the early intermediate stage in the subject.

[11] The method according to any one of [1] to [5], [7], and [8], wherein an expression level of complement component C8 that is higher than the standard level indicates the presence of arteriosclerosis at the intermediate stage in the subject.

[12] The method according to any one of [1] to [5], [7], [8], and [11], wherein an expression level of vitamin K-dependent protein Z that is higher than the standard level, indicates the presence of arteriosclerosis at the intermediate stage in the subject.

[13] The method according to any one of [1] to [12], wherein the measurement of expression is the measurement of the expression of a protein or mRNA encoding the protein.

[14] The method according to [13], wherein the expression of a protein is measured by using a substance specifically binding to the protein, or by mass spectrometry or a 2D electrophoresis method.

[15] A kit for evaluation of arteriosclerosis, comprising:
(a) a means of measuring the expression of von Willebrand factor and/or complement factor D in a sample; and
(b) a means of measuring the expression of complement component C8 and/or vitamin K-dependent protein Z in a sample.

[16] A kit for evaluation of arteriosclerosis at the early intermediate stage, comprising a means of measuring the expression of von Willebrand factor and/or complement factor D in a sample.

[17] A kit for evaluation of arteriosclerosis at the intermediate stage, comprising a means of measuring the expression of complement component C8 and/or vitamin K-dependent protein Z in a sample.

[18] The kit according to any one of [15] to [17], wherein the means for measurement is an antibody.

[19] The kit according to [18], wherein the antibody is immobilized onto a solid phase support.

[20] An apparatus for evaluation of arteriosclerosis, comprising:
(a) a means of measuring the expression of von Willebrand factor and/or complement factor D in a sample;
(b) a means of measuring the expression of complement component C8 and/or vitamin K-dependent protein Z in the sample; and
(c) a means of evaluation of arteriosclerosis in a subject based on the measurement result obtained by the means (a) and/or (b).

[21] An evaluation method for the effectiveness of a therapeutic agent or a treatment method for arteriosclerosis, comprising the steps of:
(a) measuring the expression of von Willebrand factor and/or complement factor D in a sample from an animal with arteriosclerosis treated with a test therapeutic agent or by a test treatment method;
(b) measuring the expression of complement component C8 and/or vitamin K-dependent protein Z in a sample from an animal with arteriosclerosis treated with the test therapeutic agent or by the test treatment method; and
(c) evaluating the effectiveness of the test therapeutic agent or the test treatment method against arteriosclerosis based on the results of (a) and (b).

[22] The method according to [21], further comprising a step of measuring the expression of the von Willebrand factor or complement factor D and/or the expression of complement component C8 or vitamin K-dependent protein Z in a sample from an animal with arteriosclerosis, before treatment with the test therapeutic agent or by the test treatment method.

[23] The method according to [21] or [22], wherein the animal with arteriosclerosis is a human with arteriosclerosis or an arterial disease model animal.

Effects of the Invention

The present invention enables detection of arteriosclerosis that has been missed by conventional methods in primary care or medical examination and enables assaying the possibility of the occurrence and progression of the resulting disorder. With the use of the present invention, the ratio of the expression level of a protein of a protein group contained in a sample from a subject to the expression level of the same in a standard sample and variations in the ratio over time are measured, and then the results are compared with an expression profile database compiled in advance. This makes it possible to evaluate the possibility of the occurrence of arteriosclerosis and the resulting disorder and the possibility of the progression of the symptoms. Furthermore, the present invention can be used for precisely and conveniently testing or analyzing the possibility of the occurrence of arteriosclerosis and the resulting disorder and the possibility of the progression thereof. The present invention can also be used for developing various reagents or remedies, and related apparatuses.

BRIEF DESCRIPTION OF THE DRAWINGS

FIG. 11 is a table showing the evaluation of arteriosclerosis progression stages of disease mice of another line using marker proteins selected by a mouse experiment. Each numerical value indicates the mean square sum of differences between: the logarithm of the quantitative ratio of the expression level of a protein in disease mice to the same in healthy mice; and the logarithm of the quantitative ratio of the expression level of the protein in the disease mice of another line to the same in healthy mice.

FIG. 12 shows the evaluation of arteriosclerosis progression stages of human subjects using marker proteins selected by a mouse experiment. Each numerical value indicates the mean square sum of differences between: the logarithm of the quantitative ratio of the expression level of a protein in disease mice to the same in healthy mice; and the logarithm of the quantitative ratio of the expression level of the protein in disease human subjects to the same in healthy human subjects.

EMBODIMENTS FOR CARRYING OUT THE INVENTION

Figure 1:
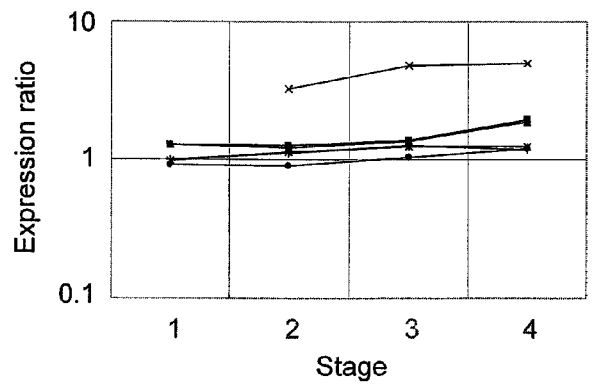
FIG. 1 shows protein group (A), the expression profile of which belongs to category 1, and graph (B) showing the expression variation patterns thereof.

The present invention is explained in detail below. This application claims a priority of Japanese patent application No. 2010-103672 filed on Apr. 28, 2010 and the content described in the description and/or drawings of this patent application is incorporated by reference.

The present invention provides novel markers and marker groups for evaluation of arteriosclerosis. The markers and marker groups provided by the present invention are proteins the expression levels of which characteristically vary with the progression of arteriosclerosis. They are useful for prediction of the onset of arteriosclerosis, determination of arteriosclerosis stages, prediction of prognosis, evaluation of therapeutic effects on arteriosclerosis existing in a subject, and evaluation of the effectiveness of therapeutic agents or treatment methods for arteriosclerosis, for example. Therefore, the method for evaluation of arteriosclerosis according to the present invention comprises the steps of: measuring the expression of a marker(s) exhibiting an expression pattern (expression variation) characteristic to a specific disease stage of arteriosclerosis in a subject-derived sample; and evaluating arteriosclerosis in the subject based on the measurement results.

In addition, the term "marker" as used herein refers to a protein to be subjected to measurement of the expression thereof for evaluation of arteriosclerosis according to the present invention or a gene (mRNA) encoding the protein. Also, the term "marker group" refers to a combination comprising two or more markers. Also, the term "expression" refers to the amount of the marker protein or a gene (mRNA) encoding the marker protein present in a sample.

Markers used in the present invention are as summarized in the following Table 1 to Table 4. In Table 1 to Table 4, the "Features" column shows the features of the expression patterns of markers described under the "Protein name" column. "Maximum at the age of 18 weeks" and "Minimum at the age of 18 weeks" under the "Features" column means that the marker exhibits the maximum expression level and the minimum expression level, respectively, in 18-week-old ApoE-deficient mice. Also, "Increasing" or "Decreasing" means that the expression level of the marker successively increases or decreases with age in weeks, but no significant variation is observed between some ages (in weeks). Moreover, "Monotonous decrease" means that the expression level of a marker decreases successively with age in weeks. Specific features of expression patterns are described later in the Description.

Furthermore, "Entry name" and "Accession No." under the "Mouse" column and the "Human" column in Table 1 to Table 4 indicate the name and accession number of a marker protein of a "mouse" and a "human" protein marker, respectively, as in the UniProtKB/Swiss-Prot (http://www.uniprot.org/).

TABLE 1

| Protein description | Features | | Mouse | | Human | | Remarks |
| --- | --- | --- | --- | --- | --- | --- | --- |
| | Male | Female | Entry name | Accession No. | Entry name | Accession No. | |
| von Willebrand factor | Maximum at 18-week-old | Maximum at 18-week-old | VWF_MOUSE | Q8CIZ8 | VWF_HUMAN | P04275 | |
| Complement factor D | Minimum at 18-week-old | Minimum at 18-week-old | CFAD_MOUSE | P03953 | CFAD_HUMAN | P00746 | |
| Complement component C8 | Increasing | Maximum at 25-week-old | CO8A_MOUSE | Q8K182 | CO8A_HUMAN | P07357 | α chain |

TABLE 1-continued

|  | Features | | Mouse | | Human | | |
|---|---|---|---|---|---|---|---|
| Protein description | Male | Female | Entry name | Accession No. | Entry name | Accession No. | Remarks |
|  |  |  | CO8B_MOUSE | Q8BH35 | CO8B_HUMAN | P07358 | β chain |
|  |  |  | CO8G_MOUSE | Q8VCG4 | CO8G_HUMAN | P07360 | γ chain |
| Vitamin K-dependent protein Z | Maximum at 25-week-old | Decreasing | PROZ_MOUSE | Q9CQW3 | PROZ_HUMAN | P22891 |  |

TABLE 2

|  | Features | | Mouse | | Human | | |
|---|---|---|---|---|---|---|---|
| Protein description | Male | Female | Entry name | Accession No. | Entry name | Accession No. | Remarks |
| CD5 antigen-like | Maximum at 18-week-old | Maximum at 25-week-old | CD5L_MOUSE | Q9QWK4 | CD5L_HUMAN | O43866 |  |
| Ig mu chain C region | Maximum at 18-week-old | Increasing | IGHM_MOUSE | P01872 | IGHM_HUMAN | P01871 |  |
| Heparin cofactor 2 | Monotonous decrease | Maximum at 18-week-old | HEP2_MOUSE | P49182 | HEP2_HUMAN | P05546 |  |
| Plasma protease C1 inhibitor | Minimum at 25-week-old |  | IC1_MOUSE | P97290 | IC1_HUMAN | P05155 |  |
| Thrombospondin-4 | Minimum at 18-25-week-old | Minimum at 25-week-old | TSP4_MOUSE | Q9Z1T2 | TSP4_HUMAN | P35443 |  |

TABLE 3

|  | Features | | Mouse | | Human | | |
|---|---|---|---|---|---|---|---|
| Protein description | Male | Female | Entry name | Accession No. | Entry name | Accession No. | Remarks |
| Alpha-2-macroglobulin | Monotonous decrease | Maximum at 18-week-old | A2M_MOUSE | Q61838 | A2MG_HUMAN | P01023 |  |
| Complement component C9 | Decreasing | Maximum at 18-week-old | CO9_MOUSE | P06683 | CO9_HUMAN | P02748 |  |
| Fetuin-B | Minimum at 18-25-week-old | Increasing | FETUB_MOUSE | Q9QXC1 | FETUB_HUMAN | Q9UGM5 |  |
| Vitamin K-dependent protein C | Monotonous decrease | Maximum at 18-week-old | PROC_MOUSE | P33587 | PROC_HUMAN | P04070 |  |

TABLE 4

|  | Features | | Mouse | | Human | | |
|---|---|---|---|---|---|---|---|
| Protein description | Male | Female | Entry name | Accession No. | Entry name | Accession No. | Remarks |
| Antithrombin-III | Decreasing | Maximum at 18-week-old | ANT3_MOUSE | P32261 | ANT3_HUMAN | P01008 |  |
| Complement C1q subcomponent subunit B | Increasing | Maximum at 18-week-old | C1QB_MOUSE | P14106 | C1QB_HUMAN | P02746 |  |
| Complement factor H | Minimum at 25-week-old | Increasing | CFAH_MOUSE | P06909 | CFAH_HUMAN | P08603 |  |
| EGF-containing fibulin-like extracellular matrix protein 1 | Monotonous decrease | Maximum at 18-week-old | FBLN3_MOUSE | Q8BPB5 | FBLN3_HUMAN | Q12805 |  |
| Inter-alpha-trypsin inhibitor heavy chain H1 | Decreasing | Maximum at 18-week-old | ITIH1_MOUSE | Q61702 | ITIH1_HUMAN | P19827 |  |
| Inter-alpha-trypsin inhibitor heavy chain H2 | Decreasing | Maximum at 18-week-old | ITIH2_MOUSE | Q61703 | ITIH2_HUMAN | P19823 |  |
| Properdin | Decreasing | Decreasing | PROP_MOUSE | P11680 | PROP_HUMAN | P27918 |  |

Proteins shown in Table 1 are markers that allow evaluation of a specific disease stage of arteriosclerosis with the use of a single marker. In the present invention, at least 1 protein from among the 4 proteins shown in Table 1 is used as a marker. In addition, "12-week-old," "18-week-old," "25-week-old," and "35-week-old" (ApoE-deficient mouse) used in tables and the Description refer to the specific disease stage corresponding to the relevant age in weeks. An association between the age in weeks of an ApoE-deficient mouse and a disease stage has been reported in Matsushima, Y. et al., J. Atheroscler.

Thromb. 8: 71-79, 2001; Nakashima, Y. et al., Arterioscler Thromb. 14: 133-140, 1994; Zhao, Y. et al., J. Nucl. Med. 49: 1707-1714, 2008, and the like. Specifically, at the age of 12 weeks, thickening of the intima of arteries and lipid accumulation are observed (stage 1). At the age of 18 weeks, foam cells are formed because of lipid accumulation (stage 2). At the age of 25 weeks, many unstable atheroplaques are observed extensively in the arteries (stage 3), corresponding to the most dangerous stage in atherosclerotic arteriosclerosis. At the age of 35 weeks, many stable lesions with advanced fibrillization and/or calcification are observed (stage 4). Therefore, in the Description, "12-week-old" (ApoE-deficient mouse) corresponds to the initial stage of arteriosclerosis, "18-week-old" corresponds to the early intermediate stage of arteriosclerosis, "25-week-old" corresponds to the intermediate stage of arteriosclerosis, and "35-week-old" corresponds to the late stage of arteriosclerosis.

Specifically, von Willebrand factor in Table 1 exhibits the maximum expression level in 18-week-old ApoE-deficient mice. Thus, whether or not arteriosclerosis is at the early intermediate stage can be evaluated based on the expression level of von Willebrand factor. Also, complement factor D in Table 1 exhibits the minimum expression level in 18-week-old ApoE-deficient mice. Thus, whether or not arteriosclerosis is at the early intermediate stage can be evaluated based on the expression level of complement factor D.

Also, complement component C8 in Table 1 exhibits an increasing tendency with the increase of the age in weeks in male ApoE-deficient mice, and it exhibits the maximum expression level in 25-week-old female ApoE-deficient mice. Thus, whether or not arteriosclerosis is at the intermediate stage can be evaluated based on the expression level thereof. Vitamin K-dependent protein Z in Table 1 exhibits the maximum expression level in 25-week-old male ApoE-deficient mice, but exhibits a decreasing tendency with the increase of age in weeks in female 25-week-old ApoE-deficient mice. Thus, whether or not arteriosclerosis is at the intermediate stage can be evaluated based on the expression level.

The present invention enables more precise and highly accurate evaluation of arteriosclerosis through the use of at least two markers in combination. Preferably, a marker exhibiting the maximum or minimum expression level in 18-week-old ApoE-deficient mice and a marker exhibiting the maximum or minimum expression level in 25-week-old ApoE-deficient mice are selected and combined. Examples of specific combinations of markers include:
(i) a combination of von Willebrand factor and complement component C8;
(ii) a combination of von Willebrand factor and vitamin K-dependent protein Z;
(iii) a combination of complement factor D and complement component C8;
(iv) a combination of complement factor D and vitamin K-dependent protein Z;
(v) a combination of von Willebrand factor, complement factor D, and complement component C8;
(vi) a combination of von Willebrand factor, complement factor D, and vitamin K-dependent protein Z;
(vii) a combination of complement factor D, complement component C8, and vitamin K-dependent protein Z; and
(viii) a combination of von Willebrand factor, complement factor D, complement component C8, and vitamin K-dependent protein Z.

Also, in the present invention, at least one marker shown in Table 1 can be combined with at least one marker selected from the markers shown in Table 2 to Table 4. Table 2 shows additional markers that are particularly preferably combined with markers shown in Table 1. Table 3 shows additional markers that are preferably combined with markers shown in Table 1. Table 4 shows additional markers that can be combined with the markers shown in Table 1. Regarding combinations of markers, arbitrary numbers and types of marker can be combined, as long as such combination contains at least one marker shown in Table 1. For example, one marker shown in Table 1 or the above combinations (i) to (viii) can be combined with one, two, three, four, or five markers shown in Table 2. Alternatively, one marker shown in Table 1 or the above combinations (i) to (viii) can also be combined with one marker shown in Table 2, one marker shown in Table 3, or one marker shown in Table 4. Such a combination can be adequately selected in accordance with subject type, sex, age, purpose of evaluation of arteriosclerosis, disease stage to be subjected to evaluation, and the like.

Alternatively, two or more types of marker shown in Table 2 to Table 4 can also be combined. For example, 2, 3, 4, 5, 10, or 15 markers shown in Table 2 to Table 4 can be combined, and preferably four markers out of those shown in Table 2 can be combined to evaluate arteriosclerosis.

As described above, the above markers or marker groups are expressed in patterns characteristic to specific disease stages of arteriosclerosis. Therefore, in the method for evaluation of arteriosclerosis according to the present invention, the expression of the above markers or marker groups in a subject-derived sample is measured. When the expression of two or more markers is measured, the steps of measuring the expression of markers can be performed simultaneously or at different times. Also, in the present invention, the term "expression of marker (group)" may refer to the expression of a marker protein, a substance derived therefrom, or a derivative thereof, or a gene (mRNA) encoding the protein. The term "substance derived therefrom" or "a derivative thereof" each refer to a substance derived or originated from a marker protein. Examples thereof include, but are not limited to, a protein containing a signal peptide, a specific subunit molecule of a protein, a modified protein, and a protein fragment. For example, complement component C8 shown in Table 1 contains $\alpha$ chain, $\beta$ chain, and $\gamma$ chain. In the present invention, the expression of an intact molecule of complement component C8 may be measured, or any one of $\alpha$ chain, $\beta$ chain, or $\gamma$ chain that is a substance derived therefrom may be measured.

Samples used herein are not particularly limited, as long as they are samples derived from subjects to be evaluated for arteriosclerosis. Samples are adequately selected in accordance with methods for measuring marker expression or types of means. Examples thereof include biological fluid samples (e.g., blood, serum, plasma, urine, saliva, tears, spinal fluid, and ascites), and tissue or cell samples (e.g., arterial tissues and cells). In view of the ease of collection, blood, serum, plasma, or the like is preferably used as a sample. When plasma is used, EDTA is preferably used as an anticoagulant, and those known or generally used in the art such as heparin and sodium citrate can be used herein. In the case of a blood sample, such sample is preferably cooled with ice or refrigerated after blood collection. Also, a tissue or cell sample is preferably frozen and cryopreserved immediately after collection by a method known or generally used in the art using liquid nitrogen, dry ice, or the like.

Also, subjects may be humans and other mammals, such as primates (e.g., monkeys and chimpanzees), domestic animals (e.g., cattle, horses, pigs, and sheep), pet animals (e.g., dogs and cats), experimental animals (e.g., mice, rats, and rabbits), and furthermore, reptiles and birds, for example.

Measurement of the expression of a marker preferably relates to semiquantitative or quantitative measurement of the amount or the concentration of the marker in a sample. The amount may be the absolute quantity or the relative quantity. Measurement can be performed directly or indirectly. Direct measurement relates to measurement of the amount or the concentration of a marker protein or mRNA existing in a sample based on a signal directly correlating with the number of molecules of the marker protein or mRNA. Such a signal is based on specific physical or chemical properties of a protein or mRNA, for example. Indirect measurement is measurement of signals obtained from secondary components (that is, marker proteins or components other than mRNA) such as antibodies, ligands (e.g., aptamers), labels, or enzymatic reaction products.

In an embodiment of the present invention, the expression of a marker protein can be measured by a means for measuring the amount of a protein in a sample. Such means are known in the art, such as immunoassay methods and reagents. Also, the expression of a marker protein can be measured by a means of measuring physical or chemical properties peculiar to the marker protein, such as a means of measuring accurate molecular weights or NMR spectra. Examples of a means of measuring the expression of a marker protein include analyzers such as a biosensor, a protein chip, an optical unit combined with immunoassay, a mass spectrometer, an NMR analyzer, a 2D electrophoresis apparatus, and a chromatography apparatus.

In a preferred embodiment, the expression of a marker protein can be measured using mass spectrometry (MS). In particular, analysis made by a mass spectrometer combined with liquid chromatography (LC/MS) is sensitive and thus is advantageous. An example of a method comprises the steps of (1) preparing protein components from a sample, (2) labeling proteins and/or peptides, (3) fractionating proteins and/or peptides, (4) subjecting proteins and/or peptides to mass spectroscopy, and (5) identifying a marker protein group from mass spectroscopic values, for example. As labels, isotope labeling reagents known in the art can be used. Appropriate labeling reagents can be commercially obtained. Also, fractionation can be performed by a method known in the art. For example, fractionation can be performed using a commercially available strong cationic column or the like.

In another embodiment, the expression of a marker protein in a sample can be measured by immunoassay (immunological assay). Specifically, the expression of a protein in a sample is measured based on a reaction between the marker protein and an antibody specifically binding to the protein. Immunoassay may be performed with either a liquid phase system or a solid phase system, as long as the method is generally employed in the art. In view of ease of detection, a solid phase system is preferably used. The forms of immunoassay are not limited and may be, in addition to a direct solid phase method, a sandwich method, a competition assay, a Western blotting method, an ELISA (enzyme linked immunosorbent assay) method, or the like.

In measurement according to the present invention, an antibody against each marker protein may be either a monoclonal antibody or a polyclonal antibody, or may be Fab, an Fv fragment, or the like capable of binding to the epitope of each marker protein. When a primary antibody and a secondary antibody are used, both antibodies may be monoclonal antibodies. Alternatively, either a primary antibody or a secondary antibody may be a polyclonal antibody. Such an antibody can be prepared by a method known in the art or can be commercially obtained.

Binding of a marker protein with an antibody can be measured according to a known method. A person skilled in the art can determine an effective and optimum measurement method for each assay according to the type and form of immunoassay to be employed, or the type of label to be used herein, for example. For example, for easy detection of the binding of a marker protein in a sample with an antibody, the binding is directly detected by labeling the antibody, or the binding is indirectly detected using a labeled secondary antibody, a biotin-avidin conjugate, or the like.

When solid-phase immunoassay is selected, a protein component in a sample can be immobilized to the solid phase, for example. A method comprising the steps of: (1) preparing protein components from a sample; (2) fractionating by SDS-polyacrylamide gel electrophoresis; (3) transferring proteins on a gel to the solid phase; (4) performing a reaction with an antibody (primary antibody) specifically binding to each marker protein; (5) washing the solid phase; (6) bringing a labeled antibody (secondary antibody) specifically binding to the primary antibody into contact with the solid phase; (7) washing the solid phase; and (8) measuring the expression level of each protein using the label, can be employed. Alternatively, an antibody may be immobilized to a solid phase. This method is referred to as namely "a sandwich method," which is broadly used as "ELISA" when an enzyme is used as a marker. A method with such a solid phase system is preferred for realizing convenient detection of a trace of protein and operation thereof.

With a solid phase system, an antibody or a protein component in a sample is immobilized onto a solid phase (e.g., a plate, a membrane, or beads), and then immunological binding of a marker protein with a solid is tested on the solid phase. Such a solid phase is not particularly limited, as long as it is conventionally used in the art. For example, a commercially available nitrocellulose membrane or PVDF membrane can be used. An antibody or a protein component in a sample is immobilized on a solid phase, so that unbound components in the sample or a reagent can be easily removed. Also, in particular, in the case of a protein array method using a membrane with dozens of types of antibody immobilized thereto, the expression of many types of marker protein can be analyzed within a short time using a small amount of a subject-derived sample (e.g., plasma). Such immunoassay can also be performed with test strips, the operation with which can be conveniently performed.

When liquid-phase immunoassay is selected, for example, a labeled antibody is brought into contact with a sample so as to bind the labeled antibody to a marker protein, the conjugate is separated, and thus the signal of the label is detected. Alternatively, an antibody (primary antibody) against a marker protein is brought into contact with a sample so as to bind a primary antibody to the marker protein, a labeled antibody (secondary antibody) is bound to the conjugate, and thus the signal of the label is detected from the conjugate of these three substances. Alternatively, for further enhancement of signals, an unlabeled secondary antibody is first bound to an antibody+marker protein conjugate, so as to bind a labeling substance to the secondary antibody. Such binding of a labeling substance to a secondary antibody can be performed by biotinylating the secondary antibody and avidinylating the labeling substance in advance, for example.

As labels for labeling antibodies to be used in immunoassay, enzymes, radio isotopes, fluorescent dyes, or avidin-biotin systems can be used. As enzymes, enzymes that are used for general enzyme immunoassay (EIA) can be used, such as peroxidase, β-galactosidase, and alkaline phosphatase. Also, an enzyme inhibition substance, a coenzyme, and the like can be used. Binding of these enzymes with antibodies can be performed by known methods using cross-linking agents such as a maleimide compound. As radio isotopes, $^{125}$I, $^{3}$H, and the like, which are used for general radio immunoassay (RIA), can be used. As fluorescent dyes, fluorescein isothiocyanate (FITC), tetramethylrhodamine isothiocyanate (TRITC), and the like, which are used for general fluorescent antibody techniques, can be used.

When a biotin-avidin complex system is used, a biotinylated antibody is reacted with a sample, and then avidin (to which a label has been added) is reacted with the thus obtained complex. Avidin can specifically bind to biotin. Through detection of the signal of a label added to avidin, binding of an antibody to a marker protein can be measured. Labels to be added to avidin are not particularly limited. For example, enzyme labels (e.g., peroxidase and alkaline phosphatase) are preferred.

The signal of a label can also be detected according to a method known in the art. For example, when an enzyme label is used, a substrate that is degraded by enzymatic action to develop color is added, the amount of the substrate degraded is optically measured to find enzyme activity, the resulting value is converted to the amount of the antibody bound, the result is compared with a standard value, and thus the amount of the antibody is calculated. A substrate differs depending on the type of enzyme to be used herein. For example, when peroxidase is used as an enzyme, 3,3',5,5'-tetramethylbenzidine can be used as a substrate, and when alkaline phosphatase is used as an enzyme, para-nitrophenol or the like can be used as a substrate. When a radioactive label is used, the radiation dose from the radioactive label is measured by a scintillation counter or the like. A fluorescent label can be detected or quantitatively determined using a fluorescent microscope, a plate reader, or the like.

Also, in the present invention, the expression of a marker protein can be measured by a means of measuring the amount of mRNA encoding the protein in a sample. Such means are known in the art, and an example thereof is primer DNA or probe DNA comprising the entire sequence or a partial sequence of DNA encoding a marker protein, or a complementary sequence thereof. The primer DNA or probe DNA specifically binds to mRNA of a marker protein expressed in a subject-derived sample or cDNA corresponding to the mRNA, so that the expression of the marker protein in the sample can be detected.

Primer DNA and probe DNA can be easily designed by a known program based on the nucleotide sequence of DNA encoding a marker protein, and can be prepared according to a method known by persons skilled in the art.

For measurement of the expression of a marker protein in a subject-derived sample, the above primer DNA and/or probe DNA is used in an amplification reaction or a hybridization reaction, and then the resulting amplified product or hybrid product is detected. When such a reaction is carried out, in general, mRNA or cDNA corresponding to the mRNA is prepared from a subject-derived sample using a method known in the art. For example, when RNA is extracted, a guanidine cesium chloride (density gradient) centrifugation method, a hot phenol method, an acid guanidine phenol chloroform (AGPC) method, or the like can be employed. cDNA can be prepared using known reverse transcriptase. The following amplification reaction and/or hybridization reaction is carried out using the above-prepared sample.

An amplification reaction is carried out using primer DNA and mRNA or cDNA as a template and then the specific amplification reaction is detected, so that the expression of a marker protein in a sample can be measured. Examples of amplification techniques include, but are not particularly limited to, known methods (e.g., PCR, RT-PCR, and real-time PCR) using the principle of the polymerase chain reaction (PCR) method. For detection of an amplified product, a known means capable of specifically recognizing an amplified product to be obtained by an amplification reaction can be used. For example, a specific amplification reaction can be detected by an agarose gel electrophoresis method or the like, so as to confirm whether or not an amplification fragment of a specific size has been amplified.

Alternatively, a labeling substance such as a radio isotope, a fluorescent substance, or a luminescent substance is caused to act on dNTP to be incorporated during the amplification reaction process, and then the labeling substance can be detected. As a radio isotope, $^{32}$P, $^{125}$I, $^{35}$S, or the like can be used. Also, as a fluorescent substance, for example, fluorescein isothiocyanate (FITC), sulforhodamine (SR), tetramethylrhodamine (TRITC), or the like can be used. As a luminescent substance, luciferin or the like can be used. The types of these labeling substances and methods for introducing these labeling substances are not particularly limited, and various conventionally known means can be used herein. An example of such a method for introducing a labeling substance is a random prime method using radio isotopes.

A method for observing an amplified product into which labeled dNTP has been incorporated may be any method as long as it is a method known in the art for detection of the above labeling substances. For example, when a radio isotope is used as a labeling substance, radioactivity can be measured using a liquid scintillation counter, a γ-counter, or the like. When a fluorescent substance is used as a labeling substance, the fluorescence can be detected using a fluorescent microscope, a fluorescent plate reader, or the like.

The expression of a marker protein can also be measured by carrying out a hybridization reaction of a sample with probe DNA, and then detecting the specific binding (hybrid). A hybridization reaction should be carried out under conditions such that probe DNA specifically binds to only mRNA or cDNA derived from a marker protein in a sample; that is, under stringent conditions. When hybridization is carried out, an appropriate label such as a fluorescent label (e.g., fluorescein or rhodamine), a radioactive label (e.g., $^{32}$P), or a biotin label can be added to probe DNA.

Detection using labeled probe DNA involves bringing a sample, or mRNA or cDNA prepared therefrom, into contact with the probe DNA so that hybridization is possible. Specifically, a sample, mRNA or cDNA is immobilized to an appropriate solid phase and then labeled probe DNA is added, or labeled probe DNA is immobilized to an appropriate solid phase and then a sample, mRNA or cDNA is added, so that the probe DNA is brought into contact with the sample, mRNA or cDNA to perform a hybridization reaction. Unhybridized probe DNA is removed, and then the label of the probe DNA hybridizing to the sample, mRNA or cDNA is detected. When the label is detected, the mRNA of the marker protein is expressed in the sample. Examples of a method for measuring the expression using labeled probe DNA include a southern hybridization method and a northern hybridization method.

As described above, the expression of a marker protein in a subject-derived sample is measured, and then arteriosclerosis in the subject can be evaluated based on the results. The term "evaluation of arteriosclerosis" as used herein refers to determination of the presence of arteriosclerosis in a subject, determination of the stage of arteriosclerosis existing in a subject, evaluation of therapeutic effects on arteriosclerosis existing in a subject, and prediction of the prognosis of arteriosclerosis existing in a subject. Also, the term "evaluation" in the present invention is meant to include continuous monitoring of arteriosclerosis that has already been evaluated or diagnosed and confirmation of the past evaluation or diagnosis of arteriosclerosis.

Persons skilled in the art understand that accurate results cannot be always obtained for all (that is, 100% of) subjects to be evaluated by the present invention (evaluation is an object of the present invention). In the present invention, the "evaluation" is intended to allow evaluation of subjects accounting for a statistically significant proportion of all subjects. Such a statistically significant proportion can be determined using various known statistical evaluation tools such as determination of a confidence interval, determination of p value, student's t-test, Mann-Whitney test, and the like. A preferable confidence interval is at least 90%. The p value is preferably 0.1, 0.01, 0.005, or 0.0001. More preferably, at least 60%, at least 80%, or at least 90% of subjects can be appropriately evaluated by the present invention.

When evaluation is performed, the expression level of a marker protein in a subject-derived sample is compared with a standard level. Such a standard level is: the measured expression level of a marker protein in a healthy-subject-derived sample, the measured expression level of a marker protein in a sample from a subject diagnosed as having arteriosclerosis at a specific stage, the measured expression level of a marker protein in a sample from a subject before treatment. A standard level for an individual subject may be varied depending on various physiological parameters such as subject type, age, and sex. Preferably, individual subjects with arteriosclerosis are classified according to the degree of the progression of the disease (stage), and samples are obtained from individual subjects belonging to each stage and individual subjects in a normal state. Then, correlations between variations in the expression of a marker protein in samples and progression stages are recorded into an expression profile database. The ratio of the expression level of a marker protein in a subject-derived sample to the same in a standard sample (prepared in advance) is measured. The expression profile database can be referred for the thus obtained measured value. Such an expression profile database is useful as "standard levels" or "standard range" that can be indicators of the presence or the absence of arteriosclerosis in a subject, the progression stage, and the onset or the degree of progression of arteriosclerosis. Such a standard level may be the only one cutoff value (e.g., average value or median value), or standard levels may be within a specific range (e.g., quartile). When evaluation is performed using a database, for example, the ratio of the expression level R(i) of a protein in a subject-derived sample to the same in a standard sample is measured. One, two, or more marker proteins (i=1-N) thereof are subjected to measurement. Each of these measured values is compared with the value at each progression stage (Rj(i), wherein "j" denotes stage No. ranging from 0-4) and then the results are recorded in the database, so that the progression stage of arteriosclerosis in the subject can be determined. Comparison can be performed by finding stage "j" at which the result of $\Sigma\{R(i)-Rj(i)\}^2 (i=1-N)$ is minimum, for example.

In addition, when evaluation is performed using a human as a subject, a standard level is also preferably the measured expression level of a marker protein in a human. As described in Example 3, a standard level obtained with the use of experimental animals such as mice can also be extrapolated.

Specific examples of evaluation of arteriosclerosis are as follows. An expression level of von Willebrand factor in a subject-derived sample that is higher than a standard level indicates the presence of arteriosclerosis at the early intermediate stage in the subject. Also, an expression level of complement factor D in a subject-derived sample that is lower than a standard level indicates the presence of arteriosclerosis at the early intermediate stage in the subject. An expression level of complement component C8 in a subject-derived sample that is higher than a standard level indicates the presence of arteriosclerosis at the intermediate stage in a subject. An expression level of vitamin K-dependent protein Z in a subject-derived sample that is higher than a standard level indicates the presence of arteriosclerosis at the intermediate stage in a subject.

Furthermore, the method for evaluation of arteriosclerosis according to the present invention may be performed in combination with other known diagnosis methods for arteriosclerosis. Examples of such known diagnosis methods for arteriosclerosis include measurement of physiological and biochemical markers of arteriosclerosis (e.g., high blood pressure, cholesterol level, and triglyceride level), measurement with electrocardiogram, measurement of arterial pulse wave velocity (PWV), and angiography.

The presence of arteriosclerosis can be determined at an early stage by the method for evaluation of arteriosclerosis according to the present invention. Specifically, the present invention enables determination of the presence or the absence of arteriosclerosis at the initial stage and the early intermediate stage, which cannot be determined by currently available diagnostic techniques or criteria. Also, when arteriosclerosis is present, the disease stage thereof can be specified in detail. Accordingly, the subject can timely receive treatment suitable for the disease stage of arteriosclerosis promptly. The method of the present invention is also advantageous in that arteriosclerosis can be reliably and rapidly evaluated at low cost.

The method for evaluation of arteriosclerosis according to the present invention can be easily and conveniently performed using a kit and/or an apparatus provided with a means of measuring the expression of the above markers.

The kit for evaluation of arteriosclerosis according to the present invention comprises at least the following means (a) or (b):
(a) a means of measuring the expression of von Willebrand factor and/or complement factor D in a sample; or
(b) a means of measuring the expression of complement component C8 and/or vitamin K-dependent protein Z in the sample.

An example of the kit of the present invention is a reagent set for mass spectroscopy, which is composed of isotope labeling reagents, mini columns for fractionation, buffers, procedure manuals, and the like, for example. Another example of the kit of the present invention is a reagent set for immunoassay, which is composed of antibody reagents against marker proteins, buffers for dilution and washing, standard antigens, labeled antibody reagents specifically binding to antibody reagents, substrate reagents for causing color development, luminescence and fluorescence generation, manuals describing procedures and evaluation methods, and the like. Antibodies contained in the kit may be antibodies that have been labeled in advance or unlabeled antibodies. Also, antibodies may be immobilized in advance to a solid phase support (e.g., a membrane or beads). Still another example of the kit of the present invention may be a kit containing a means (e.g., primer DNA and probe DNA) of measuring the expression of mRNA of a marker protein in a sample.

The kit of the present invention may contain instructions in which procedures and protocols for implementing the method of the present invention are described and tables showing standard levels or reference ranges to be employed for evaluation of arteriosclerosis, for example.

Components contained in the kit of the present invention may be individually provided or provided within a single container. Preferably, the kit of the present invention contains all the components required for implementation of the method of the present invention, as components with adjusted concentrations, for example, so that they can be used immediately.

The apparatus for evaluation of arteriosclerosis according to the present invention comprises the following means (a) and/or (b), and (c):
(a) a means of measuring the expression of von Willebrand factor and/or complement factor D in a sample;
(b) a means of measuring the expression of complement component C8 and/or vitamin K-dependent protein Z in a sample; and
(c) a means of evaluating arteriosclerosis in a subject based on the measurement results obtained by means (a) and/or (b).

The apparatus of the present invention is a system wherein the means (a) and/or (b) is combined with the means (c) so that the means can be implemented in a mutual manner, so as to be able to perform the method of the present invention.

The means (a) and/or (b) can be a measurement part for detecting and quantifying signals following the operation of a mass spectroscopy part, or a optical measurement part for detecting and quantifying or imaging signals from color development, luminescence, or fluorescence, for example. Also, the means (c) can be a data analysis part comprising software for processing measured values obtained from the measurement part and a computer, for example. A preferable apparatus is an apparatus that can be used without the knowledge of an experienced clinician. Examples of such an apparatus include test strips that require only simple addition of a sample and electronic apparatuses. A specific apparatus comprises measurement parts (e.g., a biosensor, an array, a solid phase support to which an antibody against a marker has been immobilized, mass spectrometry, a surface plasmon resonance sensor, and an NMR analyzer) and data analysis parts (e.g., a signal display part, a unit for analysis of measured values, and a computer unit).

Furthermore, the effectiveness of therapeutic agents or treatment methods for arteriosclerosis can be evaluated and candidate therapeutic agents for arteriosclerosis can be screened for by using the above markers or marker groups. Specifically, such a method of the present invention comprises the steps of:
(a) measuring the expression of von Willebrand factor and/or complement factor D in a sample from an animal with arteriosclerosis treated with a test therapeutic agent or by a test treatment method;
(b) measuring the expression of complement component C8 and/or vitamin K-dependent protein Z in a sample from an animal with arteriosclerosis treated with the test therapeutic agent or by the test treatment method; and
(c) evaluating the effectiveness of the test therapeutic agent or the test treatment method against arteriosclerosis based on the results of (a) and (b).

According to the method of the present invention, a sample is collected from an animal with arteriosclerosis, that is, an animal developing arteriosclerosis or an animal at a risk of arteriosclerosis, and the expression of a marker protein(s) in a sample is measured. Preferably, before treatment with a test therapeutic agent or by a test treatment method, a sample is collected from an animal with arteriosclerosis, the expression of a marker protein(s) in a sample is measured, and then the disease stage of arteriosclerosis is confirmed before treatment. After treatment of an animal with arteriosclerosis using a test therapeutic agent or by a test treatment method, a sample is collected at an appropriate time, and the expression of a marker protein(s) in the sample is measured. For example, samples are collected immediately after treatment, 30 minutes after, 1 hour after, 3 hours after, 5 hours after, 10 hours after, 15 hours after, 20 hours after, 24 hours (1 day) after, 2 to 10 days after, 10 to 20 days after, 20 to 30 days after, or 1 to 6 months after treatment. Collection of samples, measurement of the expression of a marker protein(s) in a sample (s), and evaluation of arteriosclerosis can be performed in a manner similar to the above.

Subject animals may be humans with arteriosclerosis, arterial disease model animals, or preferably arteriosclerosis model experimental animals (e.g., mice, rats, and rabbits), for example. In general, after confirmation of the effectiveness of a test therapeutic agent or a test treatment method in a model animal, effectiveness can be evaluated in humans by clinical trials, for example.

Types of test therapeutic agent or test treatment method for evaluation or screening are not particularly limited. For example, test therapeutic agents or test treatment methods include arbitrary material factors, specifically, naturally occurring molecules such as amino acid, peptide, oligo peptide, polypeptide, protein, nucleic acid, lipid, carbohydrate (e.g., sugar), steroid, glycopeptide, glycoprotein, and proteoglycan; synthetic analogs or derivatives of naturally occurring molecules such as peptide mimic or nucleic acid molecule (e.g., aptamer, antisense nucleic acid, and double-stranded RNA (RNAi)); molecules that do not occur naturally such as low molecular weight organic compound (e.g., inorganic and organic compound libraries, or combinatorial library); and mixtures thereof. Furthermore, a test therapeutic agent or test treatment method may be a single substance, a complex composed of a plurality of substances, a food, a feed, or the like. Moreover, test therapeutic agents or test treatment methods may be, in addition to the above material factors, radiation, ultraviolet radiation, and the like.

Procedures using a test therapeutic agent or a test treatment method with an animal differs depending on the type of therapeutic agent or treatment method, and can be easily determined by persons skilled in the art. For example, persons skilled in the art can appropriately determine administration conditions such as the dosage, the dosage period, and the route of administration of a test therapeutic agent.

Furthermore, the effectiveness of a test therapeutic agent or a test treatment method can be examined under several conditions. Examples of such conditions include the time or the period of treatment with the test therapeutic agent or by the test treatment method, the amount thereof (high or low), and frequency. For example, a dilution series of a test therapeutic agent is prepared, so that a plurality of doses can be determined.

Furthermore, when the additive effects, synergistic effects, and the like of a plurality of test therapeutic agents or test treatment methods are examined, the therapeutic agents or treatment methods may be used in combination.

The expression of a marker protein(s) in a sample of an animal after treatment with a test therapeutic agent or by a test treatment method is compared with the expression after treatment, so as to allow evaluation of whether or not the test therapeutic agent or the test treatment method is effective for improvement of arteriosclerosis (e.g., improvement from the intermediate stage to the early intermediate stage or the initial stage), or stopping or slowing down the progression of arteriosclerosis (e.g., the disease progression from the intermediate stage to the late stage is stopped, unlike a case in which no treatment has been performed).

As described above, according to the method for evaluating the effectiveness of a therapeutic agent or a treatment method for arteriosclerosis of the present invention, a therapeutic agent or a treatment method for treating or preventing arteriosclerosis can be found, and then the effectiveness of the therapeutic agent or the treatment method can be confirmed. In the case of arteriosclerosis at the early stage in particular (initial stage and the early intermediate stage), no sign indicating the disease can be detected. If a subject is evaluated as having arteriosclerosis at the initial stage or the early intermediate stage and some treatment is performed, it is difficult to evaluate the effectiveness of the treatment. Therefore, the method of the present invention is particularly effective for identifying a therapeutic agent or a treatment method effective for treatment of arteriosclerosis at the early stage.

In a manner similar to the above method, the effects of a substance or a factor on arteriosclerosis can also be determined, and thus a substance or a factor that causes the progression of arteriosclerosis can be identified.

The present invention is hereinafter illustrated in greater detail with reference to the following examples. The examples are provided merely for the explanation of the present invention and are not intended to limit or restrict the scope of the present invention disclosed in the present application. It is apparently understood that various changes and modifications to the present invention can be made based on the concept of the present invention described herein.

Example 1

ApoE-deficient (ApoED; B6·KOR/StmSlc-Apoeshl) mice, which were deficient in the lipid metabolism-related ApoE protein, were used as atherosclerosis models (Matsushima, Y. et al., J. Atheroscler. Thromb. 8: 71-79, 2001; Japan SLC, Inc.). Administration of a high-fat diet accelerates lesion progression in ApoED mice. In addition, lesion progression is accelerated depending on age in weeks. In 12-week-old mice, lesion progression is observed to such an extent that arterial intimal thickening and lipid accumulation are observed (stage 1). In 18-week-old mice, lipid accumulation results in foam cell formation (stage 2). In 25-week-old mice, many forms of unstable atherosclerotic plaque are widely observed in arteries (stage 3), and this corresponds to the most dangerous stage in the atherosclerosis process. In 35-week-old mice, many stable lesions that are highly fibrotic and calcified are observed (stage 4). Therefore, in this example, 12, 18, 25, and 35-week-old wild-type (WT; C57BL/6) mice and ApoED mice (male and female mice: 9 animals each) were subjected to blood collection. Plasma samples were prepared from the blood using 10% EDTA·2K solution.

Albumin, immunoglobulin, and transferrin in the above WT and ApoED mouse plasma samples were removed with the use of Multiple Affinity Removal Column for mouse plasma (Ms-3; 4.6×100 mm; Cat. No. 5188-5218; Agilent), followed by measurement of protein concentration and isotopic labeling with Cleavable Isotope-Coded-Affinity-Tag (cICAT) reagent (cICAT (registered trademark) Reagent 10-assay Kit; Cat. No. 4339036; Applied Biosystems).

The plasma protein fractions (1 mg each) were adjusted in a manner such that each sample contained 6M urea, 0.05% SDS, 50 mM Tris (pH 8.5), 5 mM EDTA, 10 mM TBP (final concentrations) in a total volume of 800 µl, followed by degeneration treatment at 37° C. for 30 minutes. A "Light labeling reagent" and a "Heavy labeling reagent," each of which had been dissolved with acetonitrile (200 µl), were added to a WT mouse sample and an ApoED mouse sample, respectively, followed by a labeling reaction at 37° C. for 2 hours. A 800 µl of 10 mM Tris buffer (pH 8.0) was added to each sample for pH adjustment. A trypsin solution (Trypsin, TPCK Treated; Cat. No. 4352157; Applied Biosystems) (160 µl) adjusted to 125 µg/ml was added thereto. Then, both types of samples were mixed in equivalent volumes, followed by a trypsin digestion reaction at 37° C. for 16 hours. Further, peptide fragments obtained by trypsin treatment were applied into SCX column (poly Sulfoethyl A; 4.6×100 mm; PolyLC Inc.), followed by separation of the eluate into 25 fractions. Separation was carried out with the use of an eluent A [10 mM $KH_2PO_4$ (pH 2.8), 25% ACN] and an eluent B [10 mM $KH_2PO_4$ (pH 2.8), 25% ACN, 0.5 M KCl] with a linear gradient (% B: 10 minutes-0%, 70 minutes-20%, 85 minutes-50%, 90 minutes-60%, 95 minutes-60%, and 100 minutes-100%). Each fraction was subjected to vacuum concentration so as to result in a volume that was approximately one-fourth (¼) the initial volume. Then, desalting with a desalting column (CAPCELL C18 MG; 2.0×10 mm; Shiseido) and vacuum drying were performed. An eluent A (2% ACN, 0.05% trifluoroacetic acid (TFA)) and an eluent B (80% ACN, 0.05% TFA) were used for desalting.

Each SCX fraction was analyzed using a mass spectrometry apparatus and an accompanying LC system device (NanoFrontier LD; Hitachi High-Technologies Corporation). Each obtained sample was dissolved in a buffer A (water: 98%; ACN: 2%; formic acid: 0.1%) (4 to 10 µl). One microliter of each obtained solution was applied into the apparatus. A MonoCap for Fast-flow (50 µm φ×150 mm; C18; GL Sciences) was used as a sample separation column in the LC system. Analysis was carried out with a linear gradient of buffer A and buffer B (water: 2%; ACN: 98%; formic acid: 0.1%) at a flow rate of 200 nL/min, provided that the buffer B concentration reached 2% to 30% in 120 minutes. A Monolith Trap (50 µm φ×150 mm; Cat. No. C18-50-150; Hitachi High-Technologies Corporation) was used as a trap column in the apparatus. A quartz spray chip (Picotip; outer diameter: 360 µm; inner diameter: 50 µm; tip inner diameter: 10 µm; New Objective) was used as a column tip. Electrospray ionization mass spectrometry was performed in the positive ion mode. Samples obtained from 25 fractions were subjected twice to IBA (information based acquisition) analysis. IBA is a technique involving storing target information (m/z, charge number, retention time) obtained by the first analysis in a database within an apparatus, and analyzing ions that do not correspond to the target information in the second analysis. It was expected that weak ions would be analyzed with the use of such technique so as to increase the number of identified plasma proteins. The following are additional apparatus conditions: Curtain Gas Flow: 0.7 L/min; Spray potential: 1700 V; Detector potential: 2200 V; Isolation Time: 5 ms; Isolation Width: 10 Da; and CID Time: 10 ms. The measurement data were processed using software that had been developed for ICAT comparative quantification. Thus, comparative analysis data for two groups (the WT mouse group and the ApoED mouse group) were obtained.

As a result, at least 144 proteins were confirmed to express in all 4 types (age in weeks). Regarding proteins the amounts of which in ApoE-deficient mice were increased or decreased to 1.5 or more times the amounts in WT (wild-type) mice, at least 31 proteins could be found in 18-week-old mice, for example. Furthermore, many proteins exhibiting variations characteristic to age in weeks were found. In particular, regarding proteins with expression levels that were found to be maximum or minimum during a period from the age of 18 weeks (stage 2: early intermediate stage) to the age of 25 weeks (stage 3: intermediate stage), which is suggested to relate to unstable plaque, at least 12 proteins were detected. All the above results were recorded in an expression profile database.

Figure 2:
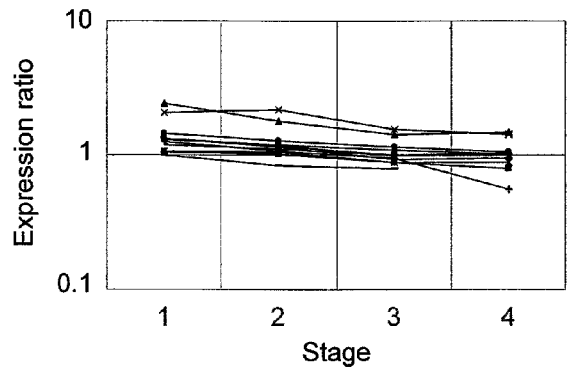
FIG. 2 shows protein group (A), the expression profile of which belongs to category 2, and graph (B) showing the expression variation patterns thereof.
Figure 3:
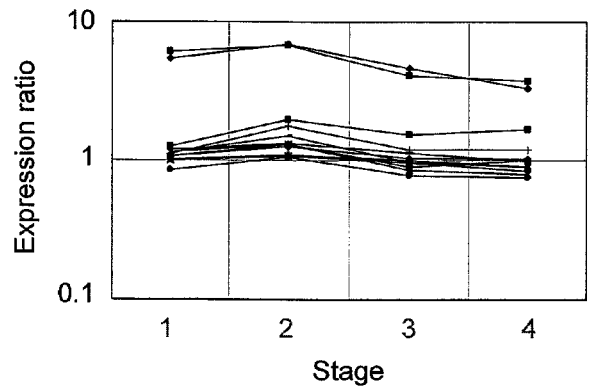
FIG. 3 shows protein group (A), the expression profile of which belongs to category 3, and graph (B) showing the expression variation patterns thereof.
Figure 4:
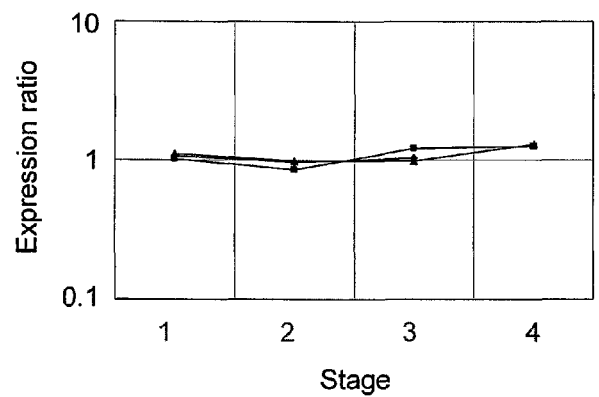
FIG. 4 shows protein group (A), the expression profile of which belongs to category 4, and graph (B) showing the expression variation patterns thereof.
Figure 5:
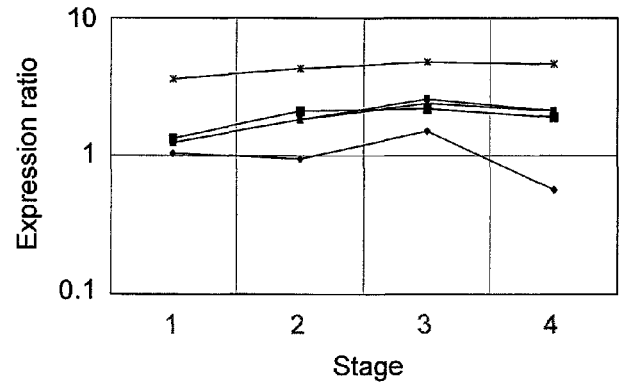
FIG. 5 shows protein group (A), the expression profile of which belongs to category 5, and graph (B) showing the expression variation patterns thereof.
Figure 6:
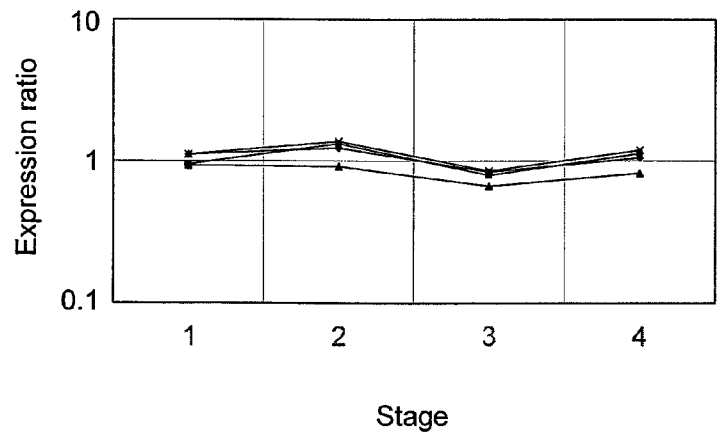
FIG. 6 shows protein group (A), the expression profile of which belongs to category 6, and graph (B) showing the expression variation patterns thereof.

With the use of these results, each protein expression ratio was plotted against lesion progression stages, and the tendencies were classified into 6 patterns (FIG. 1 to FIG. 6). In category 1 as shown in FIG. 1, proteins of a group with expression levels that were significantly increased as the stage proceeded are collected. In category 2 as shown in FIG. 2, proteins of a group, the expression levels of which were significantly decreased as the stage proceeded, are collected. In category 3 as shown in FIG. 3, proteins of a group, the expression levels of which were significantly increased when the stage proceeded from 1 to 2, significantly decreased when the stage proceeded from 2 to 3, and decreased or remained unchanged when the stage proceeded from 3 to 4, are collected. In category 4 as shown in FIG. 4, proteins of a group, the expression levels of which were significantly decreased when the stage proceeded from 1 to 2, significantly increased when the stage proceeded from 2 to 3, and increased or remained unchanged when the stage proceeded from 3 to 4, are collected. In category 5 as shown in FIG. 5, proteins of a group, the expression levels of which were increased or remained unchanged when the stage proceeded from 1 to 2, significantly increased when the stage proceeded from 2 to 3, and significantly decreased when the stage proceeded from 3 to 4, are collected. In category 6 as shown in FIG. 6, proteins of a group, the expression levels of which were decreased or remained unchanged when the stage proceeded from 1 to 2, significantly decreased when the stage proceeded from 2 to 3, and significantly increased when the stage proceeded from 3 to 4, are collected.

Figure 9:
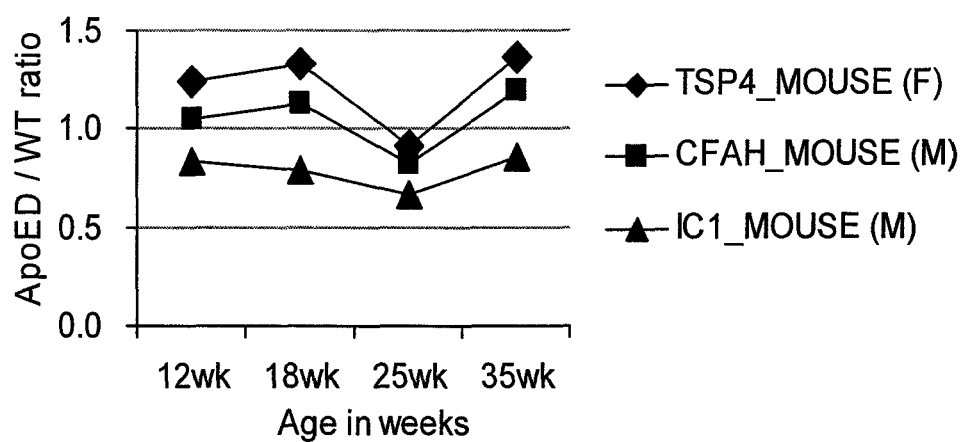
FIG. 9 shows marker proteins (A) exhibiting minimum expression levels in 25-week-old ApoE mice and graph (B) showing the expression variations thereof.
Figure 10:
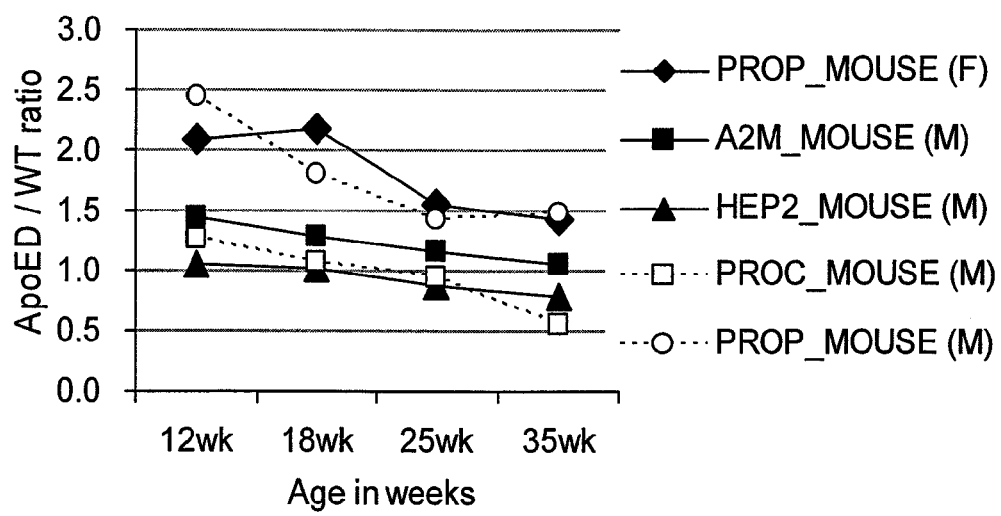
FIG. 10 shows marker proteins (A), the expression levels of which in ApoE mice were monotonously decreased with increases in age in weeks (disease stage), and graph (B) showing the expression variations thereof.
Figure 13:
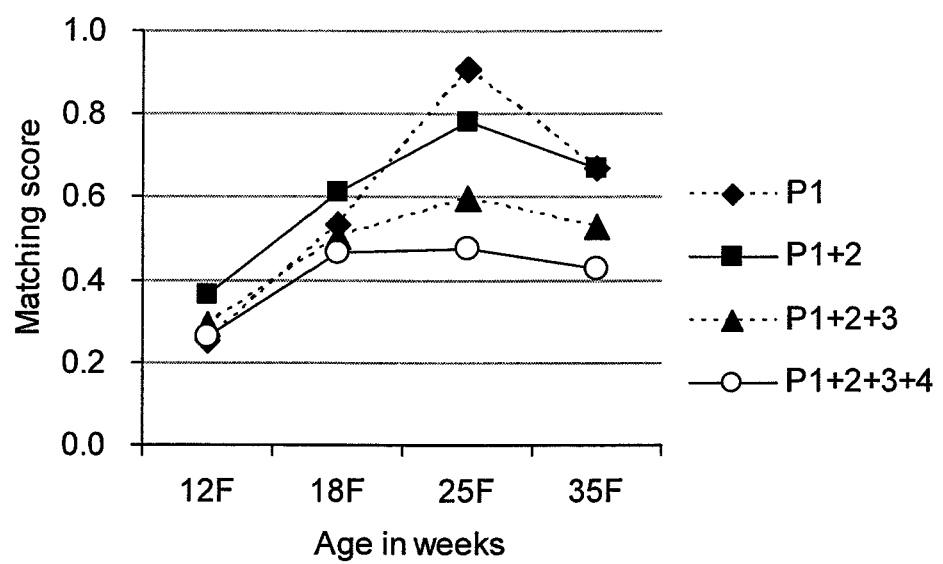
FIG. 13 is a graph showing the evaluation of the arteriosclerosis stages for female patient group F using marker combinations of P1, P1+2, P1+2+3, and P1+2+3+4.

Among proteins contained in the above expression profile database, 20 proteins exhibiting particularly significant variations were selected and then prioritized from priority No. 1 to priority No. 4 in accordance with the magnitude of variation (Table 5).

variations in expression levels of the protein group exhibiting the maximum expression levels in 18-week-old mice. FIG. 9 shows variations in expression levels of the protein group exhibiting the minimum expression levels in 25-week-old mice. FIG. 10 shows variations in expression levels of the protein group, the expression levels of which were significantly decreased as the age in weeks (disease stage) proceeded.

Example 2

In this example, arteriosclerosis of mice was actually evaluated using the markers selected in Example 1.

Blood was collected from twenty five 12-week-old ApoE knockout mice (female) (ApoEKO; B6.129P2-ApoetmlUnc/J) fed with a normal diet. Blood plasma (pool) was prepared by a method similar that described in Example 1. ApoEKO is a strain differing from ApoED described in Example 1 (Piedrahita, J A. et al., Proc. Natl. Acad. Sci. U.S.A., 89: 4471-4475, 1992; Charles River Laboratories, Japan Inc.), which

TABLE 5

| Priority | Protein description | Entry name | Mouse/female | | | | Mouse/male | | | |
| --- | --- | --- | --- | --- | --- | --- | --- | --- | --- | --- |
| | | | 12 wk | 18 wk | 25 wk | 35 wk | 12 wk | 18 wk | 25 wk | 35 wk |
| 1 | von Willebrand factor | VWF_MOUSE | 0.948 | 1.612 | 0.799 | 1.287 | 1.075 | 1.299 | 0.899 | 1.000 |
| 1 | Complement factor D | CFAD_MOUSE | 1.010 | 0.845 | 1.225 | 1.250 | 1.079 | 0.968 | 1.039 | |
| 1 | Complement component C8 alpha chain | CO8A_MOUSE | 1.241 | 1.851 | 2.584 | 2.124 | 1.281 | 1.250 | 1.377 | 1.855 |
| 1 | Complement component C8 beta chain | CO8B_MOUSE | 1.245 | 1.824 | 2.404 | 2.098 | 1.284 | 1.263 | 1.370 | 1.931 |
| 1 | Complement component C8 gamma chain | CO8G_MOUSE | 1.319 | 2.132 | 2.206 | 1.903 | 1.293 | 1.211 | 1.356 | 1.870 |
| 1 | Vitamin K-dependent protein Z | PROZ_MOUSE | 1.079 | 1.048 | 0.885 | 0.886 | 1.038 | 0.943 | 1.521 | 0.569 |
| 2 | CD5 antigen-like | CD5L_MOUSE | 3.634 | 4.341 | 4.782 | 4.613 | 5.441 | 6.885 | 4.618 | 3.306 |
| 2 | Ig mu chain C region | IGHM_MOUSE | | 3.244 | 4.815 | 5.002 | 6.114 | 6.717 | 4.114 | 3.758 |
| 2 | Heparin cofactor 2 | HEP2_MOUSE | 1.146 | 1.303 | 0.848 | 0.791 | 1.050 | 1.016 | 0.882 | 0.790 |
| 2 | Plasma protease C1 inhibitor | IC1_MOUSE | 0.835 | 0.978 | 1.026 | 0.925 | 0.838 | 0.792 | 0.664 | 0.856 |
| 2 | Thrombospondin-4 | TSP4_MOUSE | 1.235 | 1.330 | 0.912 | 1.367 | 1.112 | 0.951 | 0.935 | 1.118 |
| 3 | Alpha-2-macroglobulin | A2M_MOUSE | 1.202 | 1.321 | 1.132 | 0.983 | 1.443 | 1.278 | 1.163 | 1.059 |
| 3 | Complement component C9 | CO9_MOUSE | 1.116 | 1.760 | 1.190 | 1.204 | 1.203 | 1.105 | 1.001 | 1.000 |
| 3 | Fetuin-B | FETUB_MOUSE | 0.922 | 0.897 | 1.035 | 1.197 | 1.111 | 0.977 | 0.982 | 1.305 |
| 3 | Vitamin K-dependent protein C | PROC_MOUSE | 1.131 | 1.499 | 0.971 | 0.832 | 1.261 | 1.067 | 0.955 | 0.558 |
| 4 | Antithrombin-III | ANT3_MOUSE | 0.853 | 1.063 | 0.778 | 0.757 | 0.997 | 0.844 | 0.791 | |
| 4 | Complement C1q subcomponent subunit B | C1QB_MOUSE | 1.258 | 1.977 | 1.538 | 1.683 | 0.978 | 1.127 | 1.243 | 1.239 |
| 4 | Complement factor H | CFAH_MOUSE | 0.997 | 1.116 | 1.265 | 1.174 | 1.052 | 1.125 | 0.818 | 1.190 |
| 4 | EGF-containing fibulin-like extracellular matrix protein 1 | FBLN3_MOUSE | 1.072 | 1.263 | 1.044 | 1.010 | 1.313 | 1.196 | 1.089 | 1.013 |
| 4 | Inter-alpha-trypsin inhibitor heavy chain H1 | ITIH1_MOUSE | 1.026 | 1.094 | 1.000 | 0.900 | 1.339 | 1.159 | 0.924 | 0.951 |
| 4 | Inter-alpha-trypsin inhibitor heavy chain H2 | ITIH2_MOUSE | 0.998 | 1.077 | 0.969 | 0.896 | 1.331 | 1.165 | 0.994 | 1.039 |
| 4 | Properdin | PROP_MOUSE | 2.095 | 2.174 | 1.562 | 1.433 | 2.445 | 1.796 | 1.433 | 1.485 |

In Table 5, proteins indicated with "1" in the priority order column are proteins with which a specific arteriosclerosis stage can be evaluated by the use of each protein alone. Proteins indicated with "2," "3," or "4" in the priority order column are proteins with which arteriosclerosis can be evaluated more precisely with high accuracy by the use of each protein in combination with other marker proteins. Numerical values in Table 5 indicate quantitative ratios of the protein expression levels in 12-week-old, 18-week-old, 25-week-old, or 35-week-old disease mice (female or male) to the protein expression levels in healthy mice (female or male).

Figure 7:
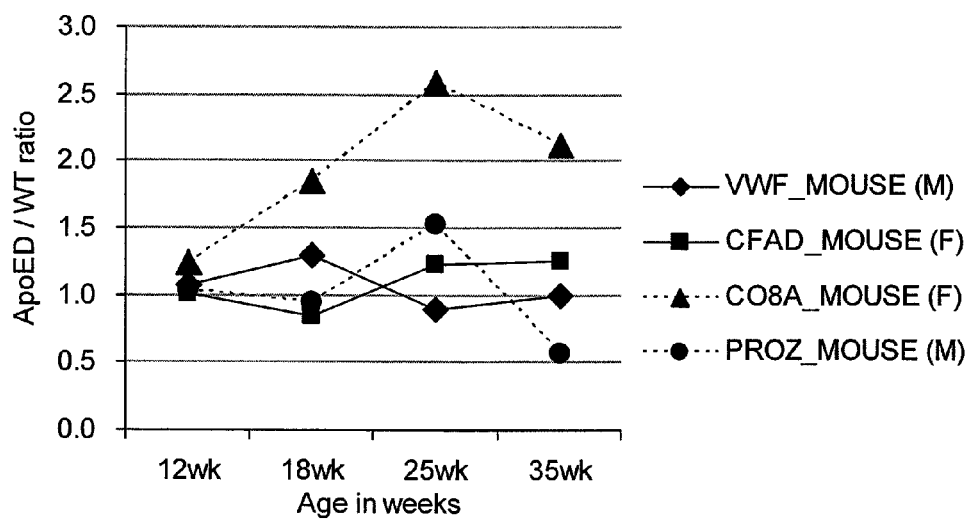
FIG. 7 shows 4 types of marker protein (A) exhibiting characteristic expression variation patterns and graph (B) showing the expression variations thereof.
Figure 8:
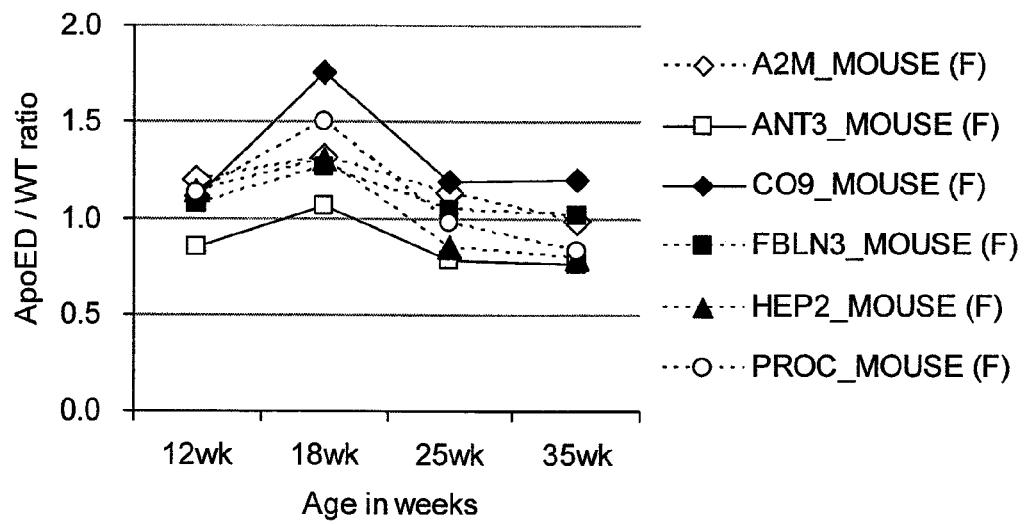
FIG. 8 shows marker proteins (A) exhibiting maximum expression levels in 18-week-old ApoE mice and graph (B) showing the expression variations thereof.

By using these results, each protein expression ratio was plotted against lesion progression stages. The tendencies were classified into a plurality of patterns (FIG. 7 to FIG. 10). FIG. 7 shows variations in expression levels of the protein group indicated with priority No. 1 in Table 5. FIG. 8 shows was confirmed in advance by preliminary examination that no lesions had been formed in arteries (data not shown). Concentrations of lipids in plasma were found to be total cholesterol of 539 mg/dl, triglyceride of 49 mg/dl, LDL cholesterol of 404 mg/dl, and HDL cholesterol of 143 mg/dl. With the standard expression level of each protein contained in plasma (pool) obtained from twenty five 12-week-old wild-type mice (WT; C57BL/6), the ratio of the expression level of each protein contained in plasma was exhaustively and quantitatively analyzed by the method described in Example 1.

FIG. 11 shows the expression ratios of 20 proteins that are in common with the protein group (Table 5) identified in Example 1. Based on these results, stages were evaluated referring to the expression profile of Example 1. Specifically, for the above 20 proteins, the square sum was calculated with differences between: the natural logarithm of each marker protein expression ratio in samples; and the natural logarithm of each marker protein expression ratio at progression stages ranging from 1 (corresponding to 12 wk) to 4 (corresponding to 35 wk) in the expression profile data. In FIG. 11, columns shown with gray indicate that a difference between the expression level of the marker and the standard expression level is high. Columns shown with dots indicate that a difference between the expression level of the marker and the standard expression level is low.

As a result, as shown in FIG. 11, when arteriosclerosis is evaluated with von Willebrand factor alone, it can be deter- Blood plasma LDL cholesterol, total cholesterol, HDL cholesterol, and triglyceride levels are as shown in Table 6. Disease group F exhibited LDL cholesterol, total cholesterol, and triglyceride levels that were higher than standard levels, but exhibited a normal HDL cholesterol level. Disease individual M exhibited LDL cholesterol, total cholesterol, HDL cholesterol, and triglyceride levels that were higher or lower than the standard levels. Disease individual M was known to have a history of arteriosclerosis as a result of questioning and was under treatment with a Zocor cholesterol-lowering agent (simvastatin).

TABLE 6

| | Sex | Age | LDL cholesterol (mg/dl) | Total cholesterol (mg/dl) | HDL cholesterol (mg/dl) | Triglyceride (mg/dl) | Remarks |
|---|---|---|---|---|---|---|---|
| Standard level | | | ≥140 | ≥220 | <40 | ≥150 | |
| Healthy group | Female | 53 ± 4 | 104 ± 14 | 182 ± 30 | 55 ± 28 | 113 ± 63 | |
| Disease group | Female | 54 ± 3 | 202 ± 70 | 317 ± 63 | 63 ± 8 | 260 ± 105 | |
| Healthy group | Male | 50 ± 3 | 104 ± 41 | 180 ± 26 | 55 ± 8 | 119 ± 45 | |
| Disease individual | Male | 51 | 153 | 296 | 36 | 536 | Cholesterol-lowering agent Zocor (simvastatin) ingestion | mined at stage 2 (corresponding to 18 wk). When arteriosclerosis is evaluated with complement factor D alone, it can be determined at stage 1 (corresponding to 12 wk). When arteriosclerosis is evaluated with complement component C8 α, β, or γ chain alone, it can always be determined at stage 1 (corresponding to 12 wk). When arteriosclerosis is evaluated with vitamin K-dependent protein Z alone, it can be determined at stage 1 (corresponding to 12 wk). Accordingly, when arteriosclerosis is evaluated with a combination of von Willebrand factor and complement component C8 α, β, or γ chain, it can be determined at stage 1 or 2 (corresponding to 12 wk or 18 wk). When arteriosclerosis is evaluated with a combination of von Willebrand factor and vitamin K-dependent protein Z, it can be determined at stage 1 or 2 (corresponding to 12 wk or 18 wk). When arteriosclerosis is evaluated with a combination of complement factor D and complement component C8 α, β, or γ chain, it can be determined at stage 1 (corresponding to 12 wk). When arteriosclerosis is evaluated with a combination of complement factor D and vitamin K-dependent protein Z, it can be determined at stage 1 (corresponding to 12 wk). Furthermore, through combination of 4 types of marker, arteriosclerosis can be determined at stage 1 or 2 (corresponding to 12 wk or 18 wk). Finally, as shown in FIG. 11, the value of each marker at stage 1 (12 wk; initial stage) was the lowest among the values at stages 1 (12 wk; initial stage), 2 (18 wk; early intermediate stage), 3 (25 wk; intermediate stage), and 4 (35 wk; late stage). Thus, the subject mouse was determined to have arteriosclerosis at most likely the progression stage 1 (12 wk; initial stage). Therefore, the effectiveness of the markers of the present invention was demonstrated.

Example 3

In this example, arteriosclerosis of human patients was actually evaluated using human proteins corresponding to the markers selected using mice in Example 1.

Purchased plasma (Biopredic International, EDTA·3K) samples collected from 3 female healthy volunteers (healthy group F) and 3 female arteriosclerosis patients (disease group F) were pooled separately. Purchased plasma (Biopredic International, EDTA·3K) samples collected from 4 male healthy volunteers (healthy group M) were also pooled. As a disease subject, a purchased plasma (Biopredic International, EDTA·3K) sample collected from 1 male arteriosclerosis patient (disease M) was prepared.

Albumin, immunoglobulin G, immunoglobulin A, transferrin, haptoglobin, and antitrypsin in the plasma samples were removed with the use of Multiple Affinity Removal Column for human plasma (Hu-6; 4.6×100 mm; Cat. No. 5188-5333; Agilent), followed by measurement of protein concentration and isotopic labeling with Cleavable Isotope-Coded-Affinity-Tag (cICAT) reagent (cICAT (registered trademark) Reagent 10-assay Kit; Cat. No. 4339036; Applied Biosystems).

The plasma protein fractions (1 mg each) were adjusted in a manner such that each sample contained 6M urea, 0.05% SDS, 50 mM Tris (pH 8.5), 5 mM EDTA, 10 mM TBP (final concentrations) in a total volume of 800 μl, followed by degeneration treatment at 37° C. for 30 minutes. A "Light labeling reagent" and a "Heavy labeling reagent," each of which had been dissolved with acetonitrile (200 μl), were added to a the healthy group and the disease (group), followed by a labeling reaction at 37° C. for 2 hours. A 800 μl of 10 mM Tris buffer (pH 8.0) was added to each sample for pH adjustment. A trypsin solution (Trypsin, TPCK Treated; Cat. No. 4352157; Applied Biosystems) (160 μl) adjusted to 125 μg/ml was added thereto. Then, both types of samples were mixed in equivalent volumes, followed by a trypsin digestion reaction at 37° C. for 16 hours. Further, peptide fragments obtained by trypsin treatment were applied into SCX column (poly Sulfoethyl A; 4.6×100 mm; PolyLC Inc.), followed by separation of the eluate into 25 fractions. Separation was carried out with the use of an eluent A [10 mM $KH_2PO_4$ (pH 2.8), 25% ACN] and an eluent B [10 mM $KH_2PO_4$ (pH 2.8), 25% ACN, 0.5 M KCl] with a linear gradient (% B: 10 minutes-0%, 70 minutes-20%, 85 minutes-50%, 90 minutes-60%, 95 minutes-60%, and 100 minutes-100%). Each fraction was subjected to vacuum concentration so as to result in a volume that was approximately one-fourth (¼) the initial volume. Then, desalting with a desalting column (CAPCELL C18 MG; 2.0× 10 mm; Shiseido) and vacuum drying were performed. An eluent A (2% ACN, 0.05% trifluoroacetic acid (TFA)) and an eluent B (80% ACN, 0.05% TFA) were used for desalting.

Each SCX fraction was analyzed using a mass spectrometry apparatus and an accompanying LC system device (NanoFrontier LD; Hitachi High-Technologies Corporation). Each obtained sample was dissolved in a buffer A (water: 98%; ACN: 2%; formic acid: 0.1%) (4 to 10 μl). One microliter of each obtained solution was applied into the apparatus. A MonoCap for Fast-flow (50 μm φ×150 mm; C18; GL Sciences) was used as a sample separation column in the LC system. Analysis was carried out with a linear gradient of a buffer A and a buffer B (water: 2%; ACN: 98%; formic acid: 0.1%) at a flow rate of 200 nL/min, provided that the buffer B concentration reached 2% to 30% in 120 minutes. A Monolith Trap (50 μm φ×150 mm; Cat. No. C18-50-150; Hitachi High-Technologies Corporation) was used as a trap column in the apparatus. A quartz spray chip (Picotip; outer diameter: 360 μm; inner diameter: 50 μm; tip inner diameter: 10 μm; New Objective) was used as a column tip. Electrospray ionization mass spectrometry was performed in the positive ion mode. Samples obtained from 25 fractions were subjected twice to IBA (information based Acquisition) analysis. IBA is a technique involving storing target information (m/z, charge number, retention time) obtained by the first analysis in a database within an apparatus, and analyzing ions that do not correspond to the target information in the second analysis. It was expected that weak ions would be analyzed with the use of such technique so as to increase the number of identified plasma proteins. The following are additional apparatus conditions: Curtain Gas Flow: 0.7 L/min; Spray potential: 1700 V; Detector potential: 2200 V; Isolation Time: 5 ms; Isolation Width: 10 Da; and CID Time: 10 ms.

The measurement data were processed using software that had been developed for ICAT comparative quantification. Thus, comparative analysis data for two groups (the healthy group and the disease (group)) were obtained. The results are shown in Table 7.

In Table 7, columns indicated with "Human female" and "Human male" indicate the quantitative ratio of the expression level of each human protein in the disease (group) to the expression level of the same in the healthy group.

TABLE 7

| Priority | Protein description | Entry name | Human/female Ratio | Human/male Ratio |
|---|---|---|---|---|
| 1 | von Willebrand factor | VWF_HUMAN | 1.433 | 1.535 |
| 1 | Complement factor D | CFAD_HUMAN | 0.576 | 0.661 |
| 1 | Complement component C8 alpha chain | CO8A_HUMAN | 0.659 | 0.783 |
| 1 | Complement component C8 beta chain | CO8B_HUMAN | 0.714 | 0.942 |
| 1 | Complement component C8 gamma chain | CO8G_HUMAN | 0.749 | 0.882 |
| 1 | Vitamin K-dependent protein Z | PROZ_HUMAN | 1.026 | 2.493 |
| 2 | CD5 antigen-like | CD5L_HUMAN | 1.132 | 1.639 |
| 2 | Ig mu chain C region | IGHM_HUMAN | 1.765 | 2.128 |
| 2 | Heparin cofactor 2 | HEP2_HUMAN | 0.66 | 0.871 |
| 2 | Plasma protease C1 inhibitor | IC1_HUMAN | 0.789 | 0.662 |
| 2 | Thrombospondin-4 | TSP4_HUMAN | 0.622 | 1.19 |
| 3 | Alpha-2-macroglobulin | A2MG_HUMAN | 0.819 | 0.572 |
| 3 | Complement component C9 | CO9_HUMAN | 0.81 | 0.657 |
| 3 | Fetuin-B | FETUB_HUMAN | 0.631 | 0.953 |
| 3 | Vitamin K-dependent protein C | PROC_HUMAN | 1.201 | 1.19 |
| 4 | Antithrombin-III | ANT3_HUMAN | 0.922 | 0.891 |
| 4 | Complement C1q subcomponent subunit B | C1QB_HUMAN | 0.723 | 0.323 |
| 4 | Complement factor H | CFAH_HUMAN | 0.859 | 0.895 |
| 4 | EGF-containing fibulin-like extracellular matrix protein 1 | FBLN3_HUMAN | 0.83 | 0.726 |
| 4 | Inter-alpha-trypsin inhibitor heavy chain H1 | ITIH1_HUMAN | 0.844 | 1.02 |
| 4 | Inter-alpha-trypsin inhibitor heavy chain H2 | ITIH2_HUMAN |  | 1.273 |
| 4 | Properdin | PROP_HUMAN | 0.86 | 0.965 |

FIG. 12 summarizes the results of calculating the mean square sum of differences between: the logarithm of the quantitative ratio (Table 5) of the expression level of each marker protein (of the marker group extracted in Example 1) in disease mice at each disease stage (age in weeks) to the expression level of the same in healthy mice; and the above-obtained logarithm (Table 7) of the quantitative ratio of the expression level of each marker protein in the disease (group) to the expression level of the same in the healthy group. Specifically, the lower the result of "(mouse at each age in weeks-human)$^2$" in FIG. 12, the stage of arteriosclerosis in question is predicted to be the stage corresponding to the mouse age in weeks.

As a result, as shown in FIG. 12, when the female patient group F is evaluated with von Willebrand factor alone, arteriolosclerosis can be determined at a stage corresponding to the mouse age of 18 weeks or 35 weeks. When the same is evaluated with complement factor D alone, arteriolosclerosis can be determined at a stage corresponding to the mouse age of 18 weeks. When the same is evaluated with complement component C8 α, β, or γ chain alone, arteriolosclerosis can be determined at a stage corresponding to the mouse age of 12 weeks in all cases. When the same is evaluated with vitamin K-dependent protein Z alone, arteriolosclerosis can be determined at a stage corresponding to the mouse age of 12 or 18 weeks. Therefore, when the female patient group F is evaluated with a combination of von Willebrand factor and complement component C8 α, β, or γ chain, arteriolosclerosis can be determined at a stage corresponding to the mouse age of 12 or 18 weeks. When the same is evaluated with a combination of von Willebrand factor with vitamin K-dependent protein Z, arteriolosclerosis can be determined at a stage corresponding to the mouse age of 12 or 18 weeks. When the same is evaluated with a combination of complement factor D and complement component C8 α, β, or γ chain, arteriolosclerosis can be determined at a stage corresponding to the mouse age of 12 or 18 weeks. When the same is evaluated with a combination of complement factor D and vitamin K-dependent protein Z, arteriolosclerosis can be determined at a stage corresponding to the mouse age of 12 or 18 weeks. Furthermore, through combination of 4 types of marker, arteriolosclerosis can be determined at a stage corresponding to the mouse age of 12 or 18 weeks. Finally, the female patient group F was evaluated as having early arteriolosclerosis at stage 1, because of the presence of many markers exhibiting the minimum mean square sum in 12-week-old mice.

To confirm that arteriosclerosis in the female patient group F can be evaluated with high accuracy through combination with other markers, the mean square sum of differences between the logarithms of the quantitative ratios was found similarly to the above for a combination (P1) of markers indicated with Priority No. 1 in Table 5, a combination (P1+2) of markers indicated with priority Nos. 1 and 2, a combination (P1+2+3) of markers indicated with priority Nos. 1 to 3, and a combination (P1+2+3+4) of markers indicated with priority Nos. 1 to 4. As a result, it was demonstrated as shown in FIG.

13, when evaluated with any combination thereof, arteriosclerosis of the female patient group F was determined at the stage corresponding to the mouse age of 12 weeks, that is, the initial stage.

In the case of male patient M, as shown in FIG. 12, when evaluated with von Willebrand factor alone, arteriolosclerosis can be determined at a stage corresponding to the mouse age of 18 weeks. When evaluated with complement component C8 α, β, or γ chain alone, arteriolosclerosis can be determined at a stage corresponding to the mouse age of 18 weeks in all cases. When evaluated with vitamin K-dependent protein Z alone, arteriolosclerosis can be determined at a stage corresponding to the mouse age of 25 weeks. Therefore, when male patient M is evaluated with a combination of von Willebrand factor and complement component C8 α, β, or γ chain, arteriolosclerosis can be determined at the stage corresponding to the mouse age of 18 weeks. When evaluated with a combination of von Willebrand factor and vitamin K-dependent protein Z, arteriosclerosis can be determined at a stage corresponding to the mouse age of 18 or 25 weeks. When evaluated with a combination of complement component C8 α, β, or γ chain and vitamin K-dependent protein Z, arteriolosclerosis can be determined at a stage corresponding to the mouse age of 18 or 25 weeks (FIG. 12). Furthermore, through evaluation with a combination of 3 markers, arteriolosclerosis can be determined at a stage corresponding to the mouse age of 18 or 25 weeks. Finally, arteriosclerosis of the male patient M was evaluated at stage 3, that is, the mid-late stage of the disease because of the presence of many markers exhibiting the minimum mean square sum in 25-week-old mice.

Figure 14:
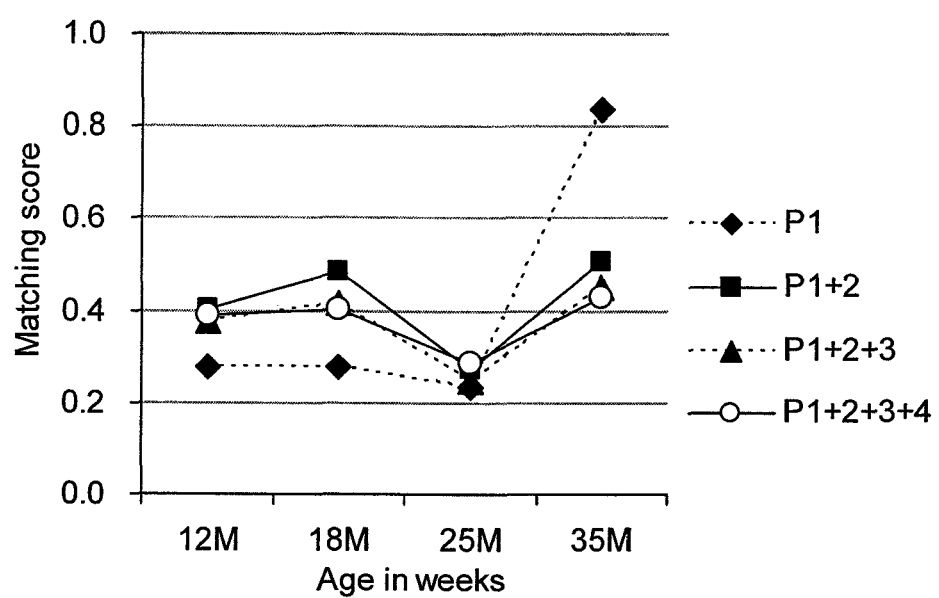
FIG. 14 is a graph showing the evaluation of the arteriosclerosis stages for male patient M using marker combinations of P1, P1+2, P1+2+3, and P1+2+3+4.

To confirm that arteriosclerosis of the male patient M can be evaluated with high accuracy through combination with other markers, the mean square sum of differences between the logarithms of the quantitative ratios was similarly found for marker combinations similar to the above, P1, P1+2, P1+2+3, and P1+2+3+4. As a result, as shown in FIG. 14, with any combination thereof, arteriosclerosis of the male patient M was always evaluated at a stage corresponding to the mouse age of 25 weeks, that is, the intermediate stage.

It was thus speculated from the above results that the female patient group F was at the initial stage of arteriosclerosis, and the male patient M was at a stage with high risk of myocardial infarction, cerebral infarction, or the like. These results were consistent with plasma lipid level or the results of questioning. Therefore, it was demonstrated that the markers identified from and the expression level data obtained from the mouse experiments in Examples 1 and 2 are also applicable to human subjects. It is predicted that human arteriosclerosis can be evaluated more precisely by creating a database of the expression levels of markers in humans.

It is apparent that the present invention can be carried out in embodiments that are not specifically mentioned in the above descriptions or in the examples. Therefore, many modifications or changes to the present invention can be made. Thus, such modifications or changes fall within the scope of the claims of the present invention.

All publications, patents, and patent applications cited herein are incorporated herein by reference in their entirety

INDUSTRIAL APPLICABILITY

According to the present invention, technology for predicting the presence or the absence of the onset of arteriosclerosis and the progression thereof is provided. The presence or the absence, the state, or the progression degree of arteriosclerosis can be conveniently determined with high accuracy by the present invention. The present invention is useful in the field of prevention or treatment of arteriosclerosis.

The invention claimed is:

1. A method for evaluation of arteriosclerosis, comprising the steps of:
    (a) measuring the expression of von Willebrand factor and/or complement factor D in a subject-derived sample;
    (b) measuring the expression of complement component C8 and/or vitamin K-dependent protein Z in the subject-derived sample; and
    (c) evaluating arteriosclerosis of the subject based on the results of (a) and (b).

2. The method according to claim 1, comprising further measuring the expression of at least one selected from the group consisting of a CD5 antigen-like protein, Ig μ chain C region, heparin cofactor 2, a plasma protease C1 inhibitor, and thrombospondin-4 in the subject-derived sample.

3. The method according to claim 1, comprising further measuring the expression of at least one selected from the group consisting of α-2-macroglobulin, complement component C9, fetuin-B, and vitamin K-dependent protein C in the subject-derived sample.

4. The method according to claim 1, comprising further measuring the expression of at least one selected from the group consisting of antithrombin-III, complement C1q subcomponent subunit B, complement factor H, EGF-containing fibrin-like extracellular matrix protein 1, inter alpha trypsin inhibitor heavy chain H1, inter alpha trypsin inhibitor heavy chain H2, and properdin in the subject-derived sample.

5. The method according to claim 1, wherein the evaluation of arteriosclerosis is determination of the presence of arteriosclerosis in the subject, determination of the stage of arteriosclerosis existing in the subject, evaluation of a therapeutic effect against arteriosclerosis existing in the subject, or prediction of prognosis of arteriosclerosis existing in the subject.

6. A method for evaluation of arteriosclerosis, comprising the steps of:
    (a) measuring the expression of complement factor D in a subject-derived sample; and
    (b) evaluating whether or not the subject has arteriosclerosis at the early intermediate stage based on the result of (a).

7. A method for evaluation of arteriosclerosis, comprising the steps of:
    (a) measuring the expression of complement component C8 and/or vitamin K-dependent protein Z in a subject-derived sample; and
    (b) evaluating whether or not the subject has arteriosclerosis at the intermediate stage based on the result of (a).

8. The method according to claim 1, wherein the evaluation step comprises comparing with a standard level selected from the measured expression level in a sample of a healthy subject, and the measured expression level in a sample of a subject with arteriosclerosis at a known stage.

9. The method according to claim 1, wherein an expression level of complement factor D that is lower than the standard level indicates the presence of arteriosclerosis at the early intermediate stage in the subject.

10. The method according to claim 1, wherein an expression level of complement component C8 that is higher than the standard level indicates the presence of arteriosclerosis at the intermediate stage in the subject.

11. The method according to claim 1, wherein an expression level of vitamin K-dependent protein Z that is higher than the standard level, indicates the presence of arteriosclerosis at the intermediate stage in the subject.

12. The method according to claim 1, wherein the measurement of expression is the measurement of the expression of a protein or mRNA encoding the protein.

13. The method according to claim 12, wherein the expression of a protein is measured by using a substance specifically binding to the protein, or by mass spectrometry or a 2D electrophoresis method.

* * * * *